(12) United States Patent
Gossen et al.

(10) Patent No.: US 8,722,875 B2
(45) Date of Patent: May 13, 2014

(54) MEANS FOR INHIBITING THE EXPRESSION OF ORC-1

(75) Inventors: Manfred Gossen, Berlin (DE); Ansgar Santel, Berlin (DE); Jorg Kaufmann, Berlin (DE)

(73) Assignee: Silence Therapeutics GmbH, Berlin (DE)

( * ) Notice: Subject to any disclaimer, the term of this patent is extended or adjusted under 35 U.S.C. 154(b) by 0 days.

(21) Appl. No.: 13/120,430

(22) PCT Filed: Sep. 23, 2009

(86) PCT No.: PCT/EP2009/054820
§ 371 (c)(1),
(2), (4) Date: Apr. 6, 2011

(87) PCT Pub. No.: WO2010/034487
PCT Pub. Date: Apr. 1, 2010

(65) Prior Publication Data
US 2011/0217367 A1    Sep. 8, 2011

(30) Foreign Application Priority Data

Sep. 23, 2008   (EP) .................................. 08016706

(51) Int. Cl.
| | | |
|---|---|---|
| *C07H 21/04* | (2006.01) | |
| *C12Q 1/68* | (2006.01) | |
| *C12N 15/11* | (2006.01) | |
| *C12N 5/02* | (2006.01) | |
| *C12N 5/00* | (2006.01) | |

(52) U.S. Cl.
USPC ........ 536/24.5; 536/23.1; 435/6.11; 435/325; 435/375; 514/44 A

(58) Field of Classification Search
None
See application file for complete search history.

(56) References Cited

U.S. PATENT DOCUMENTS 7,655,785 B1 * 2/2010 Bentwich ..................... 536/24.1
2007/0124836 A1 * 5/2007 Baum et al. .................. 800/279

FOREIGN PATENT DOCUMENTS

| EP | 1757306 A1 | 2/2007 |
| WO | WO 2005/105152 | * 11/2005 |
| WO | WO 2008/020596 | 2/2008 |
| WO | WO 2008/103971 | 8/2008 |

OTHER PUBLICATIONS

Shu, M.-Q. et al. "RNA interference targeting ORC1 gene suppresses the proliferation of vascular smooth muscle cells in rats" *Experimental and Molecular Pathology*, Jun. 1, 2008, pp. 206-212, vol. 84, No. 3.
Dhar, S. K. et al. "Replication from oriP of Epstein-Barr Virus Requires Human ORC and is Inhibited by Geminin" *Cell*, Aug. 10, 2001, pp. 287-296, vol. 106, No. 3.
Depamphilis, M. L, et al. "Cell Cycle Dependent Regulation of the Origin Recognition Complex" *Cell Cycle*, Jan. 2005, pp. 70-79, vol. 4, No. 1.
Written Opinion in International Application No. PCT/EP2009/006889, Mar. 31, 2010, pp. 1-8.

* cited by examiner

*Primary Examiner* — Doug Schultz
(74) *Attorney, Agent, or Firm* — Saliwanchik, Lloyd & Eisenschenk

(57) ABSTRACT

The present invention is related to a nucleic acid molecule comprising a double-stranded structure, whereby the double-stranded structure comprises a first strand and a second strand, whereby the first strand comprises a first stretch of contiguous nucleotides and said first stretch is at least partially complementary to a target nucleic acid, and whereby the second strand comprises a second stretch of contiguous nucleotides and said second stretch is at least partially complementary to the first stretch, whereby the first stretch comprises a nucleic acid sequence which is at least complementary to a nucleotide core sequence of the nucleic acid sequence according to SEQ ID NO: 1, whereby the nucleotide core sequence comprises the nucleotide sequence from nucleotide positions 1755 to 1763 of SEQ ID NO: 1; from nucleotide positions 1904 to 1912 of SEQ.ID.No.1; from nucleotide positions 1905 to 1913 of SEQ ID NO: 1; from nucleotide positions 2548 to 2556 of SEQ ID NO: 1; whereby the first stretch is additionally at least partially complementary to a region preceding the 5' end of the nucleotide core sequence and/or to a region following the 3' end of the nucleotide core sequence.

21 Claims, 7 Drawing Sheets

Screening of different siRNAs targeting ORC1 expression in HUVEC

HUVECs were transfected with 8 different siRNA$^{ORC1}$-lipolexes at a concentration of 20 nM for 48.

Cells were harvested and corresponding proteins extracts subjected to SDS-PAGE and processed for western blot.

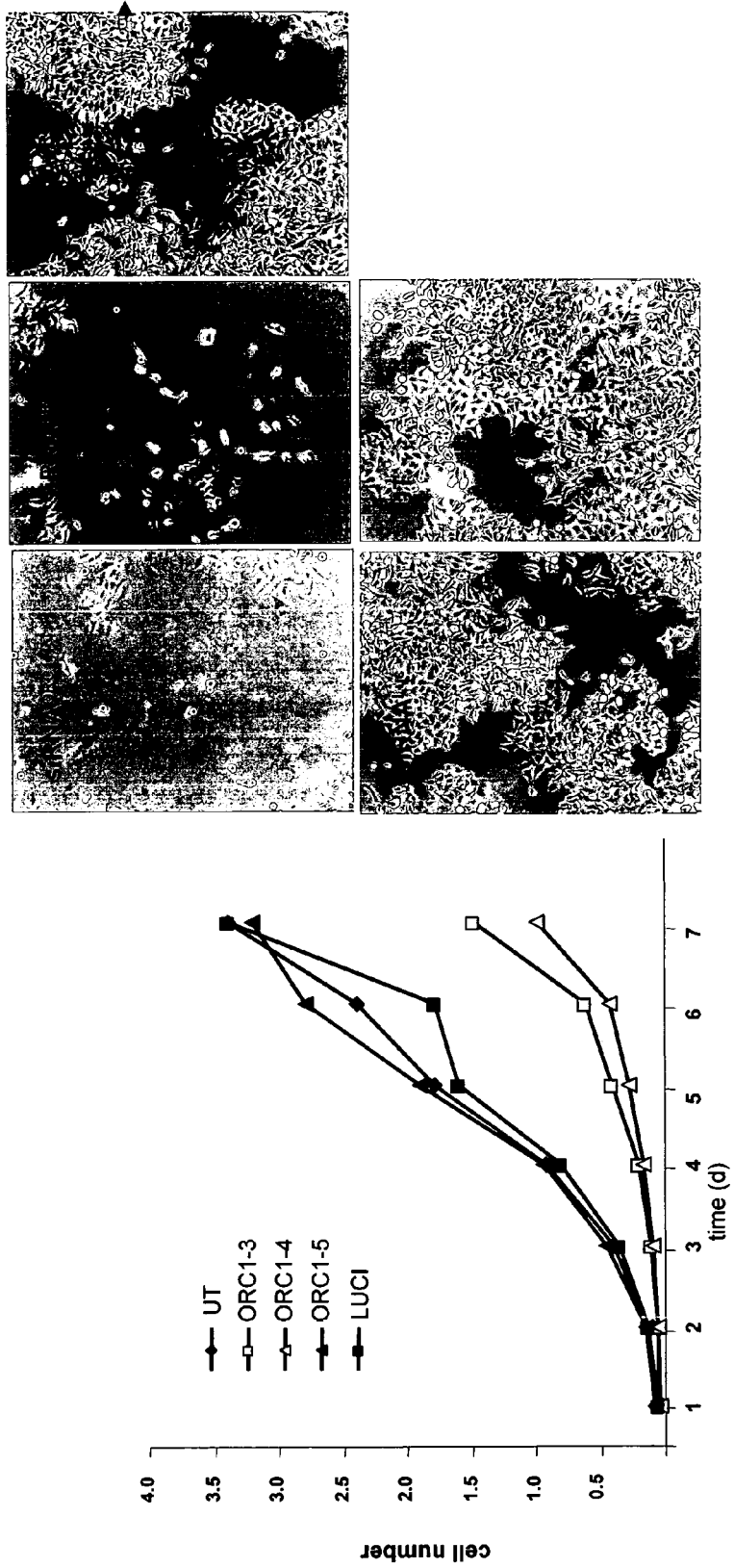

Figure 2 siRNA$^{ORC}$- lipoplexes affect proliferation of HeLa cells

A HeLa cells were transfected two highly efficacious siRNA$^{ORC1}$-lipolexes (ORC1-3; ORC1-4) and two negative control siRNA-lipoplexes and effects on proliferation were determined by cell counting. Treatment of HeLa with siRNA$^{ORC1-3}$- and siRNA$^{ORC1-4}$- lipoplexes resulted in a block of cell proliferation. Microphotographs from corresponding cell populations on day X are shown in B.

ORC1 depletion might cause inducation of apoptosis

Western blot from corresponding cells used in the proliferation experiment to demonstrate protein knockdown efficacy.

In addition, probing respective blots with anti-cleaved PARP, a marker protein for apoptosis, suggest that loss of ORC1 might induce cell death.

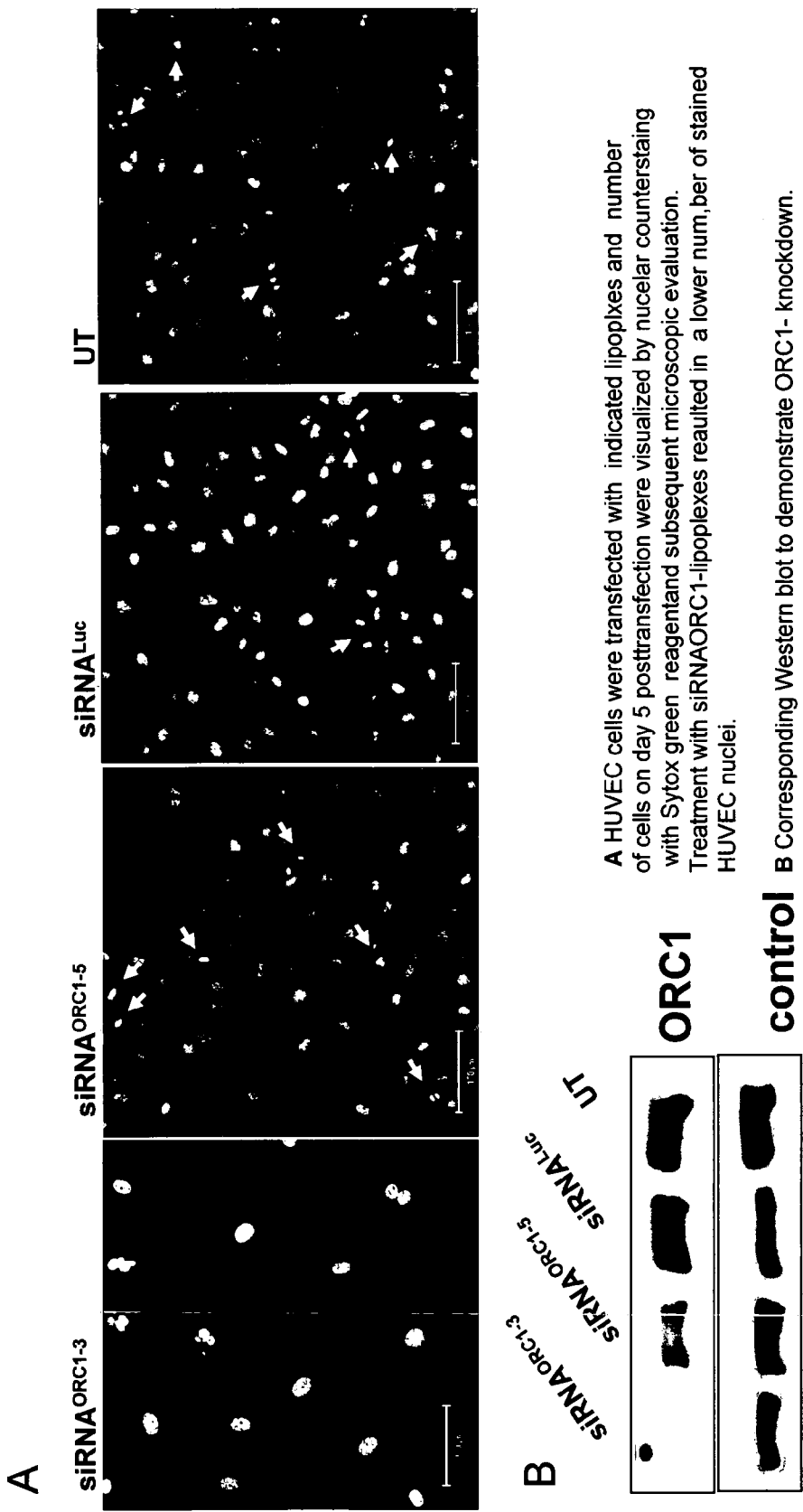

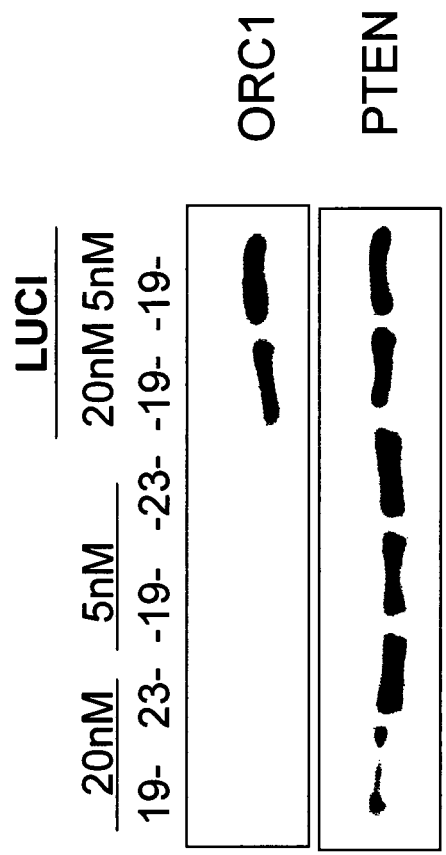

Figure 5
The 23-mer variant of siRNA^hORC1_3 is functional in HUVEC and exhibits the same knockdown efficicacy as the original 19-mer Sequence HUVEC cells were transfected with corresponding siRNA lipoplexes at indicated concentration.72h post transfection protein extracts were subjected to SDS-gel electrophoresis and ORC1 protein reduction assessed by Western blot.

siRNA^h-23-ORC1-3 (5'-3'):

A: auugaaagggaggaacaucauug-P
B: caaugauguucccuccuuucaau-P

Figure 6
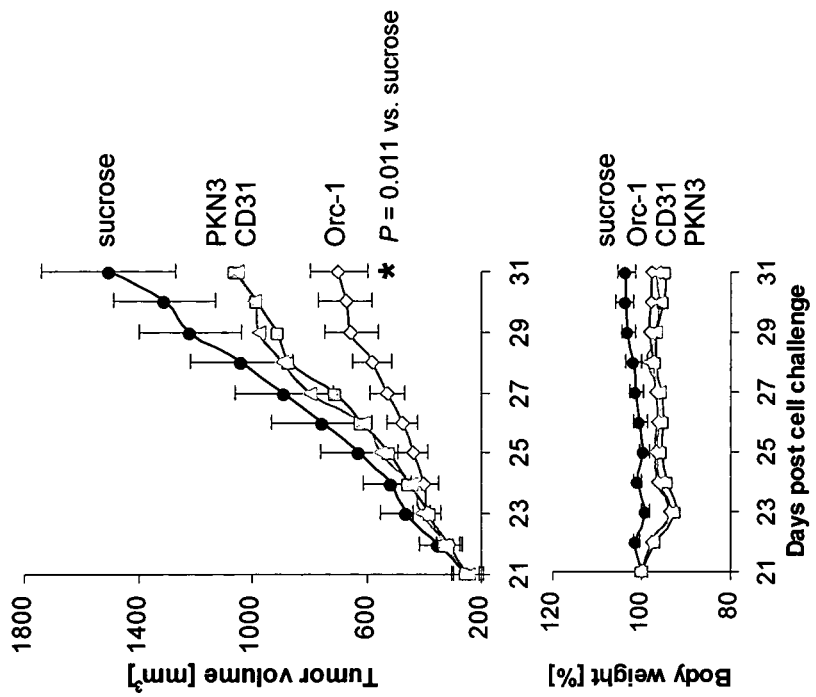
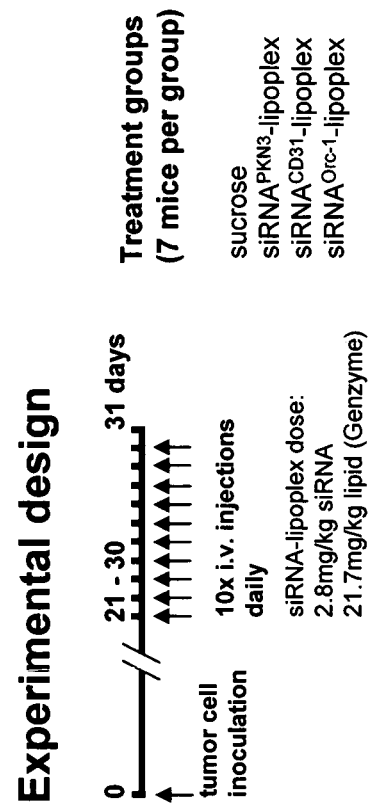
Experimental design
0 — 21 - 30 — 31 days
tumor cell inoculation
10x i.v. injections daily
siRNA-lipoplex dose:
2.8mg/kg siRNA
21.7mg/kg lipid (Genzyme)
Treatment groups
(7 mice per group)
sucrose
siRNA$^{PKN3}$-lipoplex
siRNA$^{CD31}$-lipoplex
siRNA$^{Orc-1}$-lipoplex

SEQUENCE LISTING

<160> NUMBER OF SEQ ID NOS: 71

<210> SEQ ID NO 1
<211> LENGTH: 3180
<212> TYPE: RNA
<213> ORGANISM: Homo sapiens
<220> FEATURE:
<221> NAME/KEY: mRNA
<222> LOCATION: (1)..(3180)
<223> OTHER INFORMATION: orc-1

-continued

<400> SEQUENCE: 1

| | | | | | |
|---|---|---|---|---|---|
| cggggccacg | ccgauuggcg | cgaaguuuuc | uuuucuccuu | ccaccuucuu | uucauuucua | 60 |
| gugagacaca | cgcuuugguc | cuggcuuucg | gcccguaguu | uagaaggag | cccugcuggu | 120 |
| gcagguuaga | ggugccgcau | cccccggagc | ucucgaagug | gaggcgguag | gaaacggagg | 180 |
| gcuugcggcu | agccggagga | agcuuuggag | ccggaagcca | uggcacacua | ccccacaagg | 240 |
| cugaagacca | gaaaaacuua | uucaugggguu | ggcaggcccu | uguuggaucg | aaaacugcac | 300 |
| uaccaaaccu | auagagaaau | gugugugaaa | acagaagguu | guuccaccga | gauucacauc | 360 |
| cagauuggac | aguuugucu | gauugaaggg | gaugaugaug | aaaacccgua | uguugcuaaa | 420 |
| uugcuugagu | uguucgaaga | ugacucugau | ccuccuccua | agaaacgugc | ucgaguacag | 480 |
| ugguuugucc | gauucuguga | agucccugcc | uguaaacggc | auuuguuggg | ccggaagccu | 540 |
| ggugcacagg | aaauauucug | guaugauuac | ccggccugug | acagcaacau | uaaugcggag | 600 |
| accaucauug | gccuuguucg | ggugauaccu | uuagccccaa | aggaugugu | accgacgaau | 660 |
| cugaaaaaug | agaagacacu | cuuugugaaa | cuauccugga | augagaagaa | auucaggcca | 720 |
| cuuuccucag | aacuauuugc | ggaguugaau | aaaccacaag | agagugcagc | caagugccag | 780 |
| aaacccguga | gagccaagag | uaagagugca | gagagcccuu | cuuggacccc | agcagaacau | 840 |
| guggccaaaa | ggauugaauc | aaggcacucc | gccuccaaau | cucgcaaaac | uccuacccau | 900 |
| ccucuuaccc | caagagccag | aaagaggcug | gagcuuggca | acuuagguaa | cccucagaug | 960 |
| ucccagcaga | cuucaugugc | cuccuuggau | ucuccaggaa | gaauaaaacg | gaaaguggcc | 1020 |
| uucucggaga | ucaccucacc | uucuaagaga | ucucagccug | auaaacuuca | aaccuugucu | 1080 |
| ccagcucuga | aagccccaga | gaaaaccaga | gagacuggac | ucucuuauac | ugaggaugac | 1140 |
| aagaaggcuu | caccugaaca | ucgcauaauc | cugagaaccc | gaauugcagc | uucgaaaacc | 1200 |
| auagacauua | gagaggagag | aacacuuacc | ccuaucagug | ggggacagag | aucuucagug | 1260 |
| gugccauccg | ugauucugaa | accagaaaac | aucaaaaaga | gggaugcaaa | agaagcaaaa | 1320 |
| gcccagaaug | aagcgaccuc | uacuccccau | cguauccgca | gaaagaguuc | ugucuugacu | 1380 |
| augaaucgga | uuaggcagca | gcuucgguuu | cuagguaaua | guaaaaguga | ccaagaagag | 1440 |
| aaagagauuc | ugccagcagc | agagauuuca | gacucuagca | gugacgaaga | agaggcuucc | 1500 |
| acaccgcccc | uuccaaggag | agcacccaga | acugugucca | ggaaccugcg | aucuuccuug | 1560 |
| aagucauccu | uacauacccu | cacgaaggug | ccaaagaaga | gucucaagcc | uagaacgcca | 1620 |
| cguugugccg | cuccucagau | ccguagucga | agccuggcug | cccaggagcc | agccagugug | 1680 |
| cuggaggaag | cccgacugag | gcugcaugu | ucugcguac | cugagucucu | ucccugucgg | 1740 |
| gaacaggaau | uccaagacau | cuacaauuuu | guggaaagca | aacuccuuga | ccauaccgga | 1800 |
| ggguugcaugu | acaucuccgg | ugucccuggg | acagggaaga | cugccacugu | ucaugaagug | 1860 |
| auacgcugcc | ugcagcaggc | agcccaagcc | aaugauguuc | cuccccuuca | auacauugag | 1920 |
| gucaauggca | ugaagcugac | ggagccccac | caagucuaug | ucaaaucuu | gcagaagcua | 1980 |
| acaggccaaa | aagcaacagc | caaccaugcg | gcagaacugc | uggcaaagca | auucugcacc | 2040 |
| cgagggucac | cucaggaaac | caccguccug | cuucguggaug | agcucgaccu | ucuguggacu | 2100 |
| cacaaacaag | acauaaugua | caaucucuuu | gacuggccca | cucauaagga | ggcccggcuu | 2160 |
| guggccuugg | caauugccaa | cacaauggac | cugccagagc | gaaucaugau | gaaccgggug | 2220 |
| uccagccgac | ugggucuuac | caggaugugc | uuccagcccu | auacauauag | ccagcugcag | 2280 |
| cagauccuaa | ggucccggcu | caagcaucua | aaggccuuug | aagaugaugc | cauccagcug | 2340 |

```
guagccagga agguagcagc acugucugga gaugcacgac ggugccugga caucugcagg    2400
cgugccacag agaucuguga guucucccag cagaagccug acuccccugg ccuggucacc    2460
auagcccacu caauggaagc uguggaugag auguuuucau caucauacau cacggccauc    2520
aaaaauuccu cuguucugga acagagcuuc cugagagcca uccucgcaga guuccgucga    2580
ucaggacugg aggaagccac guuucaacag auauauaguc aacauguggc acugugcaga    2640
auggagggac ugccguaccc caccauguca gagaccaugg ccgugunguuc ucaccugggc    2700 uccugucgcc uccugcuugu ggagcccagc aggaacgauc ugcuccuucg ggucgggcuc    2760
aacgucagcc aggaugaugu gcuguaugcg cugaaagacg aguaaagggg cuucacaagu    2820
uaaaagacug gggucuugcu ggguuugui uuuugagaca gggucuugcu cugucgccca    2880
ggcuggagug caguggcacg aucauggcuc acugcagccu ugacuucuca ggcuuaggug    2940
accccccaac cucauccucc cagguggcug aaacuacagg cacaugccac caugcccagc    3000
ugauuuuuug uagagacagg gcuucaccau guugccaagc uagcuacaa agcaucugau    3060 uuuggaagua cauggaauug uuguaacaaa guauauugaa uggaaauggc ucucauguau    3120
uuuggaauuu ccauuaaau aauuugcuuu uccugaaaa aaaaaaaaaa aaaaaaaaaa    3180
```

<210> SEQ ID NO 2
<211> LENGTH: 19
<212> TYPE: RNA
<213> ORGANISM: Artificial
<220> FEATURE:
<223> OTHER INFORMATION: synthetic

<400> SEQUENCE: 2
aggaauucca agacaucua                                                19

<210> SEQ ID NO 3
<211> LENGTH: 19
<212> TYPE: RNA
<213> ORGANISM: Artificial
<220> FEATURE:
<223> OTHER INFORMATION: synthetic

<400> SEQUENCE: 3
uagaugucuu ggaauuccu                                                19

<210> SEQ ID NO 4
<211> LENGTH: 19
<212> TYPE: RNA
<213> ORGANISM: Artificial
<220> FEATURE:
<223> OTHER INFORMATION: synthetic

<400> SEQUENCE: 4
gucccuggga cagggaaga                                                19

<210> SEQ ID NO 5
<211> LENGTH: 19
<212> TYPE: RNA
<213> ORGANISM: Artificial
<220> FEATURE:
<223> OTHER INFORMATION: synthetic

<400> SEQUENCE: 5
ucuucccugu cccagggac                                                19

<210> SEQ ID NO 6
<211> LENGTH: 19

```
<212> TYPE: RNA
<213> ORGANISM: Artificial
<220> FEATURE:
<223> OTHER INFORMATION: synthetic

<400> SEQUENCE: 6
gauguuccuc ccuuucaau                                              19

<210> SEQ ID NO 7
<211> LENGTH: 19
<212> TYPE: RNA
<213> ORGANISM: Artificial
<220> FEATURE:
<223> OTHER INFORMATION: synthetic

<400> SEQUENCE: 7
auugaaaggg aggaacauc                                              19

<210> SEQ ID NO 8
<211> LENGTH: 19
<212> TYPE: RNA
<213> ORGANISM: Artificial
<220> FEATURE:
<223> OTHER INFORMATION: synthetic

<400> SEQUENCE: 8
auguuccucc cuuucaaua                                              19

<210> SEQ ID NO 9
<211> LENGTH: 19
<212> TYPE: RNA
<213> ORGANISM: Artificial
<220> FEATURE:
<223> OTHER INFORMATION: synthetic

<400> SEQUENCE: 9
uauugaaagg gaggaacau                                              19

<210> SEQ ID NO 10
<211> LENGTH: 19
<212> TYPE: RNA
<213> ORGANISM: Artificial
<220> FEATURE:
<223> OTHER INFORMATION: synthetic

<400> SEQUENCE: 10
cccaccaagu cuaugugca                                              19

<210> SEQ ID NO 11
<211> LENGTH: 19
<212> TYPE: RNA
<213> ORGANISM: Artificial
<220> FEATURE:
<223> OTHER INFORMATION: synthetic

<400> SEQUENCE: 11
ugcacauaga cuugguggg                                              19

<210> SEQ ID NO 12
<211> LENGTH: 19
<212> TYPE: RNA
<213> ORGANISM: Artificial
<220> FEATURE:
<223> OTHER INFORMATION: synthetic

<400> SEQUENCE: 12
uguggacuca caaacaaga                                              19
```

```
<210> SEQ ID NO 13
<211> LENGTH: 19
<212> TYPE: RNA
<213> ORGANISM: Artificial
<220> FEATURE:
<223> OTHER INFORMATION: synthetic

<400> SEQUENCE: 13
ucuuguuugu gaguccaca                                                  19

<210> SEQ ID NO 14
<211> LENGTH: 19
<212> TYPE: RNA
<213> ORGANISM: Artificial
<220> FEATURE:
<223> OTHER INFORMATION: synthetic

<400> SEQUENCE: 14
ggaacagagc uuccugaga                                                  19

<210> SEQ ID NO 15
<211> LENGTH: 19
<212> TYPE: RNA
<213> ORGANISM: Artificial
<220> FEATURE:
<223> OTHER INFORMATION: synthetic

<400> SEQUENCE: 15
ucucaggaag cucuguucc                                                  19

<210> SEQ ID NO 16
<211> LENGTH: 19
<212> TYPE: RNA
<213> ORGANISM: Artificial
<220> FEATURE:
<223> OTHER INFORMATION: synthetic

<400> SEQUENCE: 16
ccacguuuca acagauaua                                                  19

<210> SEQ ID NO 17
<211> LENGTH: 19
<212> TYPE: RNA
<213> ORGANISM: Artificial
<220> FEATURE:
<223> OTHER INFORMATION: synthetic

<400> SEQUENCE: 17
uauaucuguu gaaacgugg                                                  19

<210> SEQ ID NO 18
<211> LENGTH: 19
<212> TYPE: RNA
<213> ORGANISM: Artificial
<220> FEATURE:
<223> OTHER INFORMATION: synthetic

<400> SEQUENCE: 18
cguacgcgga auacuucga                                                  19

<210> SEQ ID NO 19
<211> LENGTH: 19
<212> TYPE: RNA
<213> ORGANISM: Artificial
<220> FEATURE:
<223> OTHER INFORMATION: synthetic
```

```
<400> SEQUENCE: 19
ucgaaguauu ccgcguacg                                            19

<210> SEQ ID NO 20
<211> LENGTH: 23
<212> TYPE: RNA
<213> ORGANISM: Artificial
<220> FEATURE:
<223> OTHER INFORMATION: synthetic

<400> SEQUENCE: 20
caaugauguu ccucccuuuc aau                                       23

<210> SEQ ID NO 21
<211> LENGTH: 23
<212> TYPE: RNA
<213> ORGANISM: Artificial
<220> FEATURE:
<223> OTHER INFORMATION: synthetic

<400> SEQUENCE: 21
auugaaaggg aggaacauca uug                                       23

<210> SEQ ID NO 22
<211> LENGTH: 21
<212> TYPE: RNA
<213> ORGANISM: Artificial
<220> FEATURE:
<223> OTHER INFORMATION: synthetic

<400> SEQUENCE: 22
acaggaauuc caagacaucu a                                         21

<210> SEQ ID NO 23
<211> LENGTH: 21
<212> TYPE: RNA
<213> ORGANISM: Artificial
<220> FEATURE:
<223> OTHER INFORMATION: synthetic

<400> SEQUENCE: 23
uagaugucuu ggaauuccug u                                         21

<210> SEQ ID NO 24
<211> LENGTH: 23
<212> TYPE: RNA
<213> ORGANISM: Artificial
<220> FEATURE:
<223> OTHER INFORMATION: synthetic

<400> SEQUENCE: 24
gaacaggaau uccaagacau cua                                       23

<210> SEQ ID NO 25
<211> LENGTH: 23
<212> TYPE: RNA
<213> ORGANISM: Artificial
<220> FEATURE:
<223> OTHER INFORMATION: synthetic

<400> SEQUENCE: 25
uagaugucuu ggaauuccug uuc                                       23

<210> SEQ ID NO 26
<211> LENGTH: 25
```

```
<212> TYPE: RNA
<213> ORGANISM: Artificial
<220> FEATURE:
<223> OTHER INFORMATION: synthetic

<400> SEQUENCE: 26
gggaacagga auuccaagac aucua                                          25

<210> SEQ ID NO 27
<211> LENGTH: 25
<212> TYPE: RNA
<213> ORGANISM: Artificial
<220> FEATURE:
<223> OTHER INFORMATION: synthetic

<400> SEQUENCE: 27
uagaugucuu ggaauuccug uuccc                                          25

<210> SEQ ID NO 28
<211> LENGTH: 21
<212> TYPE: RNA
<213> ORGANISM: Artificial
<220> FEATURE:
<223> OTHER INFORMATION: synthetic

<400> SEQUENCE: 28
gugucccugg gacagggaag a                                              21

<210> SEQ ID NO 29
<211> LENGTH: 21
<212> TYPE: RNA
<213> ORGANISM: Artificial
<220> FEATURE:
<223> OTHER INFORMATION: synthetic

<400> SEQUENCE: 29
ucuucccugu cccagggaca c                                              21

<210> SEQ ID NO 30
<211> LENGTH: 23
<212> TYPE: RNA
<213> ORGANISM: Artificial
<220> FEATURE:
<223> OTHER INFORMATION: synthetic

<400> SEQUENCE: 30
cggugucccu gggacaggga aga                                            23

<210> SEQ ID NO 31
<211> LENGTH: 23
<212> TYPE: RNA
<213> ORGANISM: Artificial
<220> FEATURE:
<223> OTHER INFORMATION: synthetic

<400> SEQUENCE: 31
ucuucccugu cccagggaca ccg                                            23

<210> SEQ ID NO 32
<211> LENGTH: 25
<212> TYPE: RNA
<213> ORGANISM: Artificial
<220> FEATURE:
<223> OTHER INFORMATION: synthetic

<400> SEQUENCE: 32 uccgugucc cugggacagg gaaga                                           25
```

<210> SEQ ID NO 33
<211> LENGTH: 25
<212> TYPE: RNA
<213> ORGANISM: Artificial
<220> FEATURE:
<223> OTHER INFORMATION: synthetic

<400> SEQUENCE: 33
ucuucccugu cccagggaca ccgga                                      25

<210> SEQ ID NO 34
<211> LENGTH: 21
<212> TYPE: RNA
<213> ORGANISM: Artificial
<220> FEATURE:
<223> OTHER INFORMATION: synthetic

<400> SEQUENCE: 34
augauguucc ucccuuucaa u                                          21

<210> SEQ ID NO 35
<211> LENGTH: 21
<212> TYPE: RNA
<213> ORGANISM: Artificial
<220> FEATURE:
<223> OTHER INFORMATION: synthetic

<400> SEQUENCE: 35
auugaaaggg aggaacauca u                                          21

<210> SEQ ID NO 36
<211> LENGTH: 25
<212> TYPE: RNA
<213> ORGANISM: Artificial
<220> FEATURE:
<223> OTHER INFORMATION: synthetic

<400> SEQUENCE: 36
gccaaugaug uuccucccuu ucaau                                      25

<210> SEQ ID NO 37
<211> LENGTH: 25
<212> TYPE: RNA
<213> ORGANISM: Artificial
<220> FEATURE:
<223> OTHER INFORMATION: synthetic

<400> SEQUENCE: 37
auugaaaggg aggaacauca uuggc                                      25

<210> SEQ ID NO 38
<211> LENGTH: 21
<212> TYPE: RNA
<213> ORGANISM: Artificial
<220> FEATURE:
<223> OTHER INFORMATION: synthetic

<400> SEQUENCE: 38
ugauguuccu cccuuucaau a                                          21

<210> SEQ ID NO 39
<211> LENGTH: 21
<212> TYPE: RNA
<213> ORGANISM: Artificial
<220> FEATURE:
<223> OTHER INFORMATION: synthetic

```
<400> SEQUENCE: 39
uauugaaagg gaggaacauc a                                              21

<210> SEQ ID NO 40
<211> LENGTH: 23
<212> TYPE: RNA
<213> ORGANISM: Artificial
<220> FEATURE:
<223> OTHER INFORMATION: synthetic

<400> SEQUENCE: 40
aaugauguuc cucccuuuca aua                                            23

<210> SEQ ID NO 41
<211> LENGTH: 23
<212> TYPE: RNA
<213> ORGANISM: Artificial
<220> FEATURE:
<223> OTHER INFORMATION: synthetic

<400> SEQUENCE: 41
uauugaaagg gaggaacauc auu                                            23

<210> SEQ ID NO 42
<211> LENGTH: 25
<212> TYPE: RNA
<213> ORGANISM: Artificial
<220> FEATURE:
<223> OTHER INFORMATION: synthetic

<400> SEQUENCE: 42
ccaaugaugu uccuccuuu caaua                                           25

<210> SEQ ID NO 43
<211> LENGTH: 25
<212> TYPE: RNA
<213> ORGANISM: Artificial
<220> FEATURE:
<223> OTHER INFORMATION: synthetic

<400> SEQUENCE: 43
uauugaaagg gaggaacauc auugg                                          25

<210> SEQ ID NO 44
<211> LENGTH: 21
<212> TYPE: RNA
<213> ORGANISM: Artificial
<220> FEATURE:
<223> OTHER INFORMATION: synthetic

<400> SEQUENCE: 44
gccccaccaa gucuaugugc a                                              21

<210> SEQ ID NO 45
<211> LENGTH: 21
<212> TYPE: RNA
<213> ORGANISM: Artificial
<220> FEATURE:
<223> OTHER INFORMATION: synthetic

<400> SEQUENCE: 45
ugcacauaga cuuggugggg c                                              21

<210> SEQ ID NO 46
<211> LENGTH: 23
```

```
<212> TYPE: RNA
<213> ORGANISM: Artificial
<220> FEATURE:
<223> OTHER INFORMATION: synthetic

<400> SEQUENCE: 46
gagccccacc aagucuaugu gca                                              23

<210> SEQ ID NO 47
<211> LENGTH: 23
<212> TYPE: RNA
<213> ORGANISM: Artificial
<220> FEATURE:
<223> OTHER INFORMATION: synthetic

<400> SEQUENCE: 47
ugcacauaga cuuggugggg cuc                                              23

<210> SEQ ID NO 48
<211> LENGTH: 25
<212> TYPE: RNA
<213> ORGANISM: Artificial
<220> FEATURE:
<223> OTHER INFORMATION: synthetic

<400> SEQUENCE: 48
cggagcccca ccaagucuau gugca                                            25

<210> SEQ ID NO 49
<211> LENGTH: 25
<212> TYPE: RNA
<213> ORGANISM: Artificial
<220> FEATURE:
<223> OTHER INFORMATION: synthetic

<400> SEQUENCE: 49
ugcacauaga cuuggugggg cuccg                                            25

<210> SEQ ID NO 50
<211> LENGTH: 21
<212> TYPE: RNA
<213> ORGANISM: Artificial
<220> FEATURE:
<223> OTHER INFORMATION: synthetic

<400> SEQUENCE: 50
ucuguggacu cacaaacaag a                                                21

<210> SEQ ID NO 51
<211> LENGTH: 21
<212> TYPE: RNA
<213> ORGANISM: Artificial
<220> FEATURE:
<223> OTHER INFORMATION: synthetic

<400> SEQUENCE: 51
ucuuguuugu gaguccacag a                                                21

<210> SEQ ID NO 52
<211> LENGTH: 23
<212> TYPE: RNA
<213> ORGANISM: Artificial
<220> FEATURE:
<223> OTHER INFORMATION: synthetic

<400> SEQUENCE: 52
cuucugugga cucacaaaca aga                                              23
```

```
<210> SEQ ID NO 53
<211> LENGTH: 23
<212> TYPE: RNA
<213> ORGANISM: Artificial
<220> FEATURE:
<223> OTHER INFORMATION: synthetic

<400> SEQUENCE: 53
ucuuguuugu gaguccacag aag                                           23

<210> SEQ ID NO 54
<211> LENGTH: 25
<212> TYPE: RNA
<213> ORGANISM: Artificial
<220> FEATURE:
<223> OTHER INFORMATION: synthetic

<400> SEQUENCE: 54
accuucugug gacucacaaa caaga                                         25

<210> SEQ ID NO 55
<211> LENGTH: 25
<212> TYPE: RNA
<213> ORGANISM: Artificial
<220> FEATURE:
<223> OTHER INFORMATION: synthetic

<400> SEQUENCE: 55
ucuuguuugu gaguccacag aaggu                                         25

<210> SEQ ID NO 56
<211> LENGTH: 21
<212> TYPE: RNA
<213> ORGANISM: Artificial
<220> FEATURE:
<223> OTHER INFORMATION: synthetic

<400> SEQUENCE: 56
cuggaacaga gcuuccugag a                                             21

<210> SEQ ID NO 57
<211> LENGTH: 21
<212> TYPE: RNA
<213> ORGANISM: Artificial
<220> FEATURE:
<223> OTHER INFORMATION: synthetic

<400> SEQUENCE: 57
ucucaggaag cucuguucca g                                             21

<210> SEQ ID NO 58
<211> LENGTH: 23
<212> TYPE: RNA
<213> ORGANISM: Artificial
<220> FEATURE:
<223> OTHER INFORMATION: synthetic

<400> SEQUENCE: 58
uucuggaaca gagcuuccug aga                                           23

<210> SEQ ID NO 59
<211> LENGTH: 23
<212> TYPE: RNA
<213> ORGANISM: Artificial
<220> FEATURE:
<223> OTHER INFORMATION: synthetic
```

```
<400> SEQUENCE: 59
ucucaggaag cucuguucca gaa                                          23

<210> SEQ ID NO 60
<211> LENGTH: 25
<212> TYPE: RNA
<213> ORGANISM: Artificial
<220> FEATURE:
<223> OTHER INFORMATION: synthetic

<400> SEQUENCE: 60
uguucuggaa cagagcuucc ugaga                                        25

<210> SEQ ID NO 61
<211> LENGTH: 25
<212> TYPE: RNA
<213> ORGANISM: Artificial
<220> FEATURE:
<223> OTHER INFORMATION: synthetic

<400> SEQUENCE: 61
ucucaggaag cucuguucca gaaca                                        25

<210> SEQ ID NO 62
<211> LENGTH: 21
<212> TYPE: RNA
<213> ORGANISM: Artificial
<220> FEATURE:
<223> OTHER INFORMATION: synthetic

<400> SEQUENCE: 62
agccacguuu caacagauau a                                            21

<210> SEQ ID NO 63
<211> LENGTH: 21
<212> TYPE: RNA
<213> ORGANISM: Artificial
<220> FEATURE:
<223> OTHER INFORMATION: synthetic

<400> SEQUENCE: 63
uauaucuguu gaaacguggc u                                            21

<210> SEQ ID NO 64
<211> LENGTH: 23
<212> TYPE: RNA
<213> ORGANISM: Artificial
<220> FEATURE:
<223> OTHER INFORMATION: synthetic

<400> SEQUENCE: 64
gaagccacgu uucaacagau aua                                          23

<210> SEQ ID NO 65
<211> LENGTH: 23
<212> TYPE: RNA
<213> ORGANISM: Artificial
<220> FEATURE:
<223> OTHER INFORMATION: synthetic

<400> SEQUENCE: 65
uauaucuguu gaaacguggc uuc                                          23

<210> SEQ ID NO 66
<211> LENGTH: 25
```

-continued

```
<212> TYPE: RNA
<213> ORGANISM: Artificial
<220> FEATURE:
<223> OTHER INFORMATION: synthetic

<400> SEQUENCE: 66
aggaagccac guuucaacag auaua                                            25

<210> SEQ ID NO 67
<211> LENGTH: 25
<212> TYPE: RNA
<213> ORGANISM: Artificial
<220> FEATURE:
<223> OTHER INFORMATION: synthetic

<400> SEQUENCE: 67
uauaucuguu gaaacguggc uuccu                                            25

<210> SEQ ID NO 68
<211> LENGTH: 19
<212> TYPE: RNA
<213> ORGANISM: Artificial
<220> FEATURE:
<223> OTHER INFORMATION: synthetic

<400> SEQUENCE: 68
uuuggacuca caaacaaga                                                   19

<210> SEQ ID NO 69
<211> LENGTH: 19
<212> TYPE: RNA
<213> ORGANISM: Artificial
<220> FEATURE:
<223> OTHER INFORMATION: synthetic

<400> SEQUENCE: 69
ucuuguuugu gaguccaaa                                                   19

<210> SEQ ID NO 70
<211> LENGTH: 19
<212> TYPE: RNA
<213> ORGANISM: Artificial
<220> FEATURE:
<223> OTHER INFORMATION: synthetic

<400> SEQUENCE: 70
caaccuuuca acagauaua                                                   19

<210> SEQ ID NO 71
<211> LENGTH: 19
<212> TYPE: RNA
<213> ORGANISM: Artificial
<220> FEATURE:
<223> OTHER INFORMATION: synthetic

<400> SEQUENCE: 71
uauaucuguu gaaagguug                                                   19
```

MEANS FOR INHIBITING THE EXPRESSION OF ORC-1

CROSS-REFERENCE TO RELATED APPLICATION

This application is the U.S. national stage application of International Patent Application No. PCT/EP2009/006889, filed Sep. 23, 2009.

The present invention is related to double-stranded nucleic acid molecules suitable to inhibit the expression of Orc-1 and the use thereof Cancer is fundamentally a genetic disease in which damage to cellular DNA leads to disruption of the normal mechanisms that control cellular proliferation. Two of the mechanisms of action by which tumor suppressors maintain genomic integrity is by cell arrest, thereby allowing the repair of damaged DNA, or removal of the damaged DNA by apoptosis (Ellisen and Haber, Ann. Rev. Med, 1998, 49, 425.436; Evan and Littlewood, Science 1998, 281, 1317-1322. Apoptosis, otherwise called "programmed cell death," is a carefully regulated network of biochemical events which act as a cellular suicide program aimed at removing irreversibly damaged cells. Apoptosis can be triggered in a number of ways including binding of tumor necrosis factor, DNA damage, withdrawal of growth factors, and antibody cross-linking of Fas receptors. Although several genes have been identified that play a role in the apoptotic process, the pathways leading to apoptosis have not been fully elucidated. Many investigators have attempted to identify novel apoptosis-promoting genes with the objective that such genes would afford a means to induce apoptosis selectively in neoplastic cells to treat cancer in a patient.

An alternative approach to treating cancer involves the suppression of angiogenesis with an agent such as Endostatin™ or anti-VEGF antibodies. Following this approach, the objective is to prevent further vascularization of the primary tumor and potentially to constrain the size of metastatic lesions to that which can support neoplastic cell survival without substantial vascular growth.

Another approach which may be followed in treatment of cancer is to affect replication of tumor cells.

Replication licensing in eukaryotes is a multi-step process taking place at origins of DNA replication on the chromosome. It prepares the chromosomes for the initiation of DNA replication in the next S-phase of the cell cycle. DNA replication initiation is followed by DNA replication elongation and finally DNA replication termination. Licensing itself takes place in the preceding M- and G1 phase. It involves the successive recruitment of a series of proteins, collectively referred to as preRC proteins (pre-replicative complex). Specifically, these are the six Ore proteins Orc-1, -2, -3, -4, -5, -6, forming the so-called heterohexameric ORC (origin recognition complex), Cdc6 and cdt1, the six Mcm proteins Mcm2, -3, -4, -5, -6, -7, forming the so-called MCM complex(es).

These major subgroups are listed in the general order of their recruitment. However, there are several uncertainties about details of the timing for some of the proteins.

ORC is supposed to make the initial chromosome contacts, thereby defining the localisation of the origin; the MCM complex is the likely DNA helicase for melting of the origin region and possibly also the replicative DNA helicase. Individual steps of the preRC assembly process seem to be mainly controlled by cell cycle kinase activities, which also activate preRC before DNA replication commences.

There is a longstanding interest in interfering with DNA replication for the purpose of combating cancer. The principal idea is that in the adult body the majority of cells is quiescent, i.e. they neither replicate their DNA nor do they proliferate. Both these features are characteristics of cancer cells. Any intervention in the DNA replication process would thus have a greater impact on a tumor as compared to the "host" organism. Therapeutic approaches interfering with DNA replication could thus be viewed as differential poisoning of the organism. This has been achieved by numerous chemotherapeutic regimens with their well established benefits but also drawbacks. Generally speaking, most of these small molecule therapeutics target enzymatic activities required for DNA replication at its elongation phase such as, e.g., topoisomerase inhibitors. For the time being no small molecule inhibitors interfering with the preRC assembly exist, aside from indirectly acting inhibitors of cyclin dependent kinases. The high proliferation rate of tumor cells also sparked interest in the use of proteins involved in DNA replication, including preRC proteins, as diagnostic markers. A comprehensive outline on DNA replication and cancer and cancer diagnosis can be found in "DNA Replication and Human Disease" (*Cold Spring Harbor Monograph Series* 47), edited By Melvin L. DePamphilis, *National Institutes of Health*.

In the lights of this, there is an ongoing need in the art for means for the treatment of neoplastic diseases and of means which allow such treatments.

The problem underlying the present invention is solved by the subject matter of the attached independent claims. Preferred embodiments may be taken from the dependent claims.

More specifically, the problem underlying the present invention is solved in a first aspect which is also a first embodiment, by a nucleic acid molecule comprising a double-stranded structure, whereby the double-stranded structure comprises a first strand and a second strand, whereby the first strand comprises a first stretch of contiguous nucleotides and said first stretch is at least partially complementary to a target nucleic acid, and whereby the second strand comprises a second stretch of contiguous nucleotides and said second stretch is at least partially complementary to the first stretch, whereby the first stretch comprises a nucleic acid sequence which is at least complementary to a nucleotide core sequence of the nucleic acid sequence according to SEQ.ID.No. 1, whereby the nucleotide core sequence comprises the nucleotide sequence from nucleotide positions 1755 to 1763 of SEQ.ID.No 1;

from nucleotide positions 1904 to 1912 of SEQ.ID.No.1;

from nucleotide positions 1905 to 1913 of SEQ.ID.No.1;

from nucleotide positions 2548 to 2556 of SEQ.ID.No.1 whereby the first stretch is additionally at least partially complementary to a region preceding the 5' end of the nucleotide core sequence and/or to a region following the 3' end of the nucleotide core sequence.

In a second embodiment of the first aspect which is also an embodiment of the first embodiment of the first aspect, the first stretch is complementary to the nucleotide core sequence.

In a third embodiment of the first aspect which is also an embodiment of the first and the second embodiment of the first aspect, the first stretch is additionally complementary to the region following the 3' end of the nucleotide core sequence.

In a fourth embodiment of the first aspect which is also an embodiment of the first, second and third embodiment of the first aspect, the first stretch is complementary to the target nucleic acid over 18 to 29 nucleotides, preferably 19 to 25 nucleotides and more preferably 19 to 23 nucleotides.

In a fifth embodiment of the first aspect which is also an embodiment of the fourth embodiment of the first aspect, the nucleotides are consecutive nucleotides.

In a sixth embodiment of the first aspect which is also an embodiment of the first, second, third, fourth and fifth embodiment of the first aspect, the first stretch and/or the second stretch comprises from 18 to 29 consecutive nucleotides, preferably 19 to 25 consecutive nucleotides and more preferably 19 to 23 consecutive nucleotides.

In a seventh embodiment of the first aspect which is also an embodiment of the first, second, third, fourth, fifth and sixth embodiment of the first aspect, the first strand consists of the first stretch and/or the second strand consists of the second stretch.

The problem underlying the present invention is solved in a second aspect which is also a first embodiment of the second aspect and an embodiment of the first aspect, by a nucleic acid molecule, preferably a nucleic acid molecule according to the first aspect, comprising a double-stranded structure, whereby the double-stranded structure is formed by a first strand and a second one strand, whereby the first strand comprises a first stretch of contiguous nucleotides and the second strand comprises a second stretch of contiguous nucleotides and whereby said first stretch is at least partially complementary to said second stretch, whereby the first stretch consists of a nucleotide sequence according to SEQ.ID.Nos: 2, 22, 24 or 26, and the second stretch consists of a nucleotide sequence according to SEQ.ID.Nos: 3, 23, 25 or 27;
  the first stretch consists of a nucleotide sequence according to SEQ.ID.Nos: 6, 34, 20 or 36 and the second stretch consists of a nucleotide sequence according to SEQ.ID.Nos: 7, 35, 21 or 37;
  the first stretch consists of a nucleotide sequence according to SEQ.ID.Nos: 8, 38, 40 or 42, and the second stretch consists of a nucleotide sequence according to SEQ.ID.Nos: 9, 39, 41 or 43;
  the first stretch consists of a nucleotide sequence according to SEQ.ID.Nos: 12, 50, 52 or 54, and the second stretch consists of a nucleotide sequence according to SEQ.ID.Nos: 13, 51, 53 or 55;
  the first stretch consists of a nucleotide sequence according to SEQ.ID.Nos: 14, 56, 58, 60, and the second stretch consists of a nucleotide sequence according to SEQ.ID.Nos.: 15, 57, 59 or 61, whereby preferably the stretch is identical to the strand in term of nucleotide sequence and/or length.

In a second embodiment of the second aspect which is also an embodiment of the first embodiment of the first aspect and an embodiment of the first aspect, the first stretch and/or the second stretch comprises a plurality of groups of modified nucleotides having a modification at the 2' position, whereby within the stretch each group of modified nucleotides is flanked on one or both sides by a flanking group of nucleotides, whereby the flanking nucleotide(s) forming the flanking group of nucleotides is/are either an unmodified nucleotide or a nucleotide having a modification different from the modification of the modified nucleotides, whereby preferably the first stretch and/or the second stretch comprises at least two groups of modified nucleotides and at least two flanking groups of nucleotides.

In a third embodiment of the second aspect which is also an embodiment of the first and the second embodiment of the second aspect and an embodiment of the first aspect, the first stretch and/or the second stretch comprises a pattern of groups of modified nucleotides and/or a pattern of flanking groups of nucleotides, whereby the pattern is a positional pattern.

In a fourth embodiment of the second aspect which is also an embodiment of the first, the second and the third embodiment of the second aspect and an embodiment of the first aspect, preferably of the embodiments of the first aspect and the first embodiment of the second aspect the first stretch and/or the second stretch comprise at the 3' end a dinucleotide, whereby such dinucleotide is preferably TT.

In a fifth embodiment of the second aspect which is also an embodiment of the fourth embodiment of the second aspect the length of the first stretch and/or of the second stretch consists of 19 to 23 nucleotides, preferably 19 to 21 nucleotides.

In a sixth embodiment of the second aspect which is also an embodiment of the first, second, third, fourth and fifth embodiment of the second aspect and an embodiment of the first aspect and its various embodiments, preferably embodiments 1 to 7 of the first aspect and the first embodiment of the second aspect, the first and/or the second stretch comprise an overhang of 1 to 5 nucleotides at the 3' end.

In a seventh embodiment of the second aspect which is also an embodiment of the sixth embodiment of the second aspect the length of the double-stranded structure is from about 16 to 27 nucleotide pairs, preferably 19 to 23 nucleotide pairs.

In an eighth embodiment of the second aspect which is also an embodiment of the seventh embodiment of the second aspect the first strand and the second strand are covalently linked to each other, preferably the 3' end of the first strand is covalently linked to the 5' end of the second strand.

The problem underlying the present invention is solved in a third aspect which is also a first embodiment of the third-aspect, by a lipoplex comprising a nucleic acid according to any of embodiments of the first and the second aspect, and a liposome.

In a second embodiment of the third aspect which is also an embodiment of the first embodiment of the third aspect, the liposome consists of:

In a second embodiment of the third aspect which is also an embodiment of the first embodiment of the third aspect, the liposome consists of
  a) about 50 mol % β-arginyl-2,3-diaminopropionic acid-N-palmityl-N-oleyl-amide trihydrochloride, preferably (β-(L-arginyl)-2,3-L-diaminopropionic acid-N-palmityl-N-oleyl-amide tri-hydrochloride);
  b) about 48 to 49 mol % 1,2-diphytanoyl-sn-glycero-3-phosphoethanolamine (DPhyPE); and
  c) about 1 to 2 mol % 1,2-distearoyl-sn-glycero-3-phosphoethanolamine-polyethylen-glycole, preferably N-(Carbonyl-methoxypolyethyleneglycol-2000)-1,2-distearoyl-sn-glycero-3-phosphoethanolamine sodium salt.

In a third embodiment of the third aspect which is also an embodiment of the first and the second embodiment of the third aspect, the zeta-potential of the lipoplex is about 40 to 55 mV, preferably about 45 to 50 mV.

In a fourth embodiment of the third aspect which is also an embodiment of the second and third embodiment of the third aspect, the lipoplex has a size of about 80 to 200 nm, preferably of about 100 to 140 nm, and more preferably of about 110 nm to 130 nm, as determined by QELS.

The problem underlying the present invention is solved in a fourth aspect which is also a first embodiment of the fourth aspect, by a vector, preferably an expression vector, comprising or coding for a nucleic acid according to any embodiment t of the first and the second aspect.

The problem underlying the present invention is solved in a fifth aspect which is also a first embodiment of the fifth aspect, by a cell comprising a nucleic acid according to any embodiment of the first and the second aspect of the preceding claims or vector according to any embodiment of the fourth aspect, whereby, preferably, if the cell is a human cell said human cell is an isolated cell.

The problem underlying the present invention is solved in a sixth aspect which is also a first embodiment of the sixth aspect, by a composition, preferably a pharmaceutical composition, comprising a nucleic acid according to any embodiment of the first and second aspect, a lipoplex according to any embodiment of the third aspect, a vector according to any aspect of the fourth aspect and/or a cell according to any embodiment of the fifth aspect.

In a second embodiment of the sixth aspect which is also an embodiment of the first embodiment of the sixth aspect, the composition is a pharmaceutical composition optionally further comprising a pharmaceutically acceptable vehicle.

In a third embodiment of the sixth aspect which is also an embodiment of the first and the second embodiment of the sixth aspect, the composition is a pharmaceutical composition and said pharmaceutical composition is for the treatment of a proliferative disease and/or of a DNA virus infection based viral disease.

In a fourth embodiment of the sixth aspect which is also an embodiment of the third embodiment of the sixth aspect, the proliferative disease or cancer disease is selected from the group comprising all malignancies such as carcinomas, sarcomas, hematopoietic malignancies, and germ cell tumors, and including bladder cancer, melanoma, breast cancer, non-Hodgkin lymphoma, colon and rectal cancer, pancreatic cancer, endometrial cancer, prostate cancer, kidney or renal cell cancer, non-melanoma skin cancer, leukemia, thyroid cancer, lung cancer, neurofibromatosis, all diseases related to vascular proliferation including non-physiological endothelial proliferation, atherosclerosis, adenoma, angiofibroma, arachnoid cysts, astrocytoma, bone neoplasms, Bowen's disease, breast cyst, breast neoplasms, breast neoplasms, male, Burkitt lymphoma, carcinoid tumor, carcinoma, carcinoma, Merkel cell carcinoma, non-small-cell lung carcinoma, small cell lung carcinoma, cementoma, choledochal cyst, chondroma, chondrosarcoma, chordoma, craniopharyngioma, cysts, dermoid cyst, digestive system neoplasms, ear neoplasms, endocrine gland neoplasms, endometrial neoplasms, ependymoma, epidermal cyst, fibromatosis, aggressive, fibromatosis, juvenile hyaline (not on MeSH), gastrointestinal neoplasms, gastrointestinal stromal tumors, genital neoplasms, female, genital neoplasms, male, glioblastoma, glioma, hamartoma, hamartoma syndrome, multiple, head and neck neoplasms, hemangioma, histiocytoma, benign fibrous, histiocytoma, malignant fibrous, Hodgkin disease, Hutchinson's melanotic freckle, insulinoma, Krukenberg tumor, laryngeal neoplasms, leiomyoma, leiomyosarcoma, leukemia, lipoma, lung neoplasms, lymphangioma, lymphoma, lymphoma, non-Hodgkin, mediastinal cyst, medulloblastoma, melanoma, melanoma, amelanotic, meningioma, mesothelioma, mouth neoplasms, multiple myeloma, myoma, myxoma, neoplasm metastasis, neoplasm, residual, neoplasms, neoplasms, connective and soft tissue, nervous system neoplasms, neurilemmoma, neuroblastoma, neuroendocrine tumors, neuroma, acoustic, nevus, odontogenic tumors, osteosarcoma, otorhinolaryngologic neoplasms, ovarian cysts, ovarian neoplasms, Paget's disease, mammary, papilloma, paraganglioma, paraneoplastic syndromes, nervous system, pheochromocytoma, pilonidal sinus, popliteal cyst, precancerous conditions, pseudomyxoma peritonei, ranula, rectal neoplasms, respiratory tract neoplasms, retinoblastoma, rhabdoid tumor, rhabdomyosarcoma, sarcoma, sarcoma, Ewing's, Sezary syndrome, skin neoplasms, Tarlov cysts, teratoma, thymoma, tonsillar neoplasms, tuberous sclerosis, urologic neoplasms, uterine cervical dysplasia, uterine cervical neoplasms, Wilms tumor, vulvar neoplasms, benign prostatic hyperplasia, breast hyperplasia including atypical usual ductal hyperplasia, compensatory liver hyperplasia, congenital adrenal hyperplasia, endometrial hyperplasia including polycystic ovary syndrome and endometrial adenocarcinoma, focal epithelial hyperplasia, Heck's disease, and sebaceous hyperplasia.

In a fifth embodiment of the sixth aspect which is also an embodiment of the third and fourth embodiment of the sixth aspect, the viral disease is selected from the group comprising, Bell palsy, Burkitt lymphoma, chickenpox, cytomegalovirus infections, eethyma, contagious, encephalitis, herpes simplex, Epstein-Barr virus infections, erythema infectiosum, exanthema subitum, herpes labialis, herpes simplex, herpes zoster, herpes zoster oticus, Herpesviridae infections, infectious mononucleosis, molluscum contagiosum, polyomavirus infections, smallpox, warts, human papillomavirus HPV, infectious mononucleosis, EBV-associated malignancies including but not limited to nasopharyngeal carcinoma and chronic fatigue syndrome; and, for KSHV Kaposi's sarcoma.

The problem underlying the present invention is solved in a seventh aspect which is also a first embodiment of the seventh aspect, by the nucleic acid according to any embodiments of the first and second aspect, the lipoplex according to any embodiment of the third aspect, the vector according to any aspect of the fourth aspect and/or the cell according to any embodiment of the fifth aspect for use in a method for treating a subject in need of such treating and suffering from or being at risk of suffering from a disease.

In a second embodiment of the seventh aspect which is also an embodiment of the first embodiment of the seventh aspect, the disease is any disease as defined in connection with the embodiments of the sixth aspect.

The problem underlying the present invention is solved in an eighth aspect which is also a first embodiment of the eighth aspect, by the use of a nucleic acid according to any embodiments of the first and second aspect, of a lipoplex according to any embodiment of the third aspect, of a vector according to any embodiment of the fourth aspect and/or a cell according to any embodiment of the fifth aspect for the manufacture of a medicament.

In a second embodiment of the eighth aspect which is also an embodiment of the first embodiment of the eighth aspect, the medicament is for the treatment of any of the diseases as defined in connection with any embodiment of the sixth aspect.

In a third embodiment of the eighth aspect which is also an embodiment of the second embodiment of the eighth aspect, the medicament is used in combination with one or several other therapies.

In a fourth embodiment of the eighth aspect which is also an embodiment of the second embodiment of the eighth aspect, the medicament is used in combination with oncolytic and/or antiviral first-line therapy, oncolytic and/or antiviral second-line therapy and/or oncolytic and/or antiviral third-line therapy. As preferably used herein, a first-line therapy is the first treatment for a disease or a condition. In patients with cancer, first-line therapy can be surgery, chemotherapy, radiation therapy, or a combination of these therapies. Second-line therapy as preferably used herein is treatment given when initial treatment and more specifically first-line therapy does not work or stops working. Third-line therapy as preferably used herein is treatment given when the initial and/or the second-line therapy does not work or stops working.

In a fifth embodiment of the eighth aspect which is also an embodiment of the third and fourth embodiment of the eighth aspect, the therapy is selected from the group comprising chemotherapy, cryotherapy, hyperthermia, antibody therapy and radiation therapy.

In a sixth embodiment of the eighth aspect which is also an embodiment of the first embodiment of the eighth aspect, the therapy is antibody therapy and more preferably an antibody therapy using an anti-VEGF antibody.

The present inventors have also realized that there is a conceptual advantage of addressing DNA replication in the treatment of cancer.

Such conceptual advantage of targeting the DNA replication initiation process as compared to the more conventional strategy of interfering with elongation resides in the specificity aspect. Proteins involved in elongation routinely participate in DNA repair and recombination. Therefore, their inhibition can easily cause genomic instability. Contrary to that, the proteins of the preRC are apparently not involved in chromosome transactions other than DNA replication initiation. Thus, their inhibition is expected to have less long-term side effects on the organism.

Of further interest is the apparent lack of redundancy in all the genes encoding preRC proteins. Each of them is therefore essential for DNA replication and cells should have no way to bypass the lack of one of these proteins given it can be down-regulated sufficiently.

While several studies firmly established the correlation of cdc6 and MCM protein levels with proliferation, this is not obvious for ORC proteins, as several of them apparently persist in quiescent cell cultures or even in differentiated tissues of the mouse as may be taken from Madine M A et al. (J Struct Biol. 2000 April; 129(2-3):198-210) or Huang Z. et al (J Cell Biol. 2005 Aug. 15; 170(4):527-35).

Orc-1 is not a constitutive integral part of ORC, but rather a transient interaction partner, reflecting its cell cycle regulatory role for DNA replication licensing as also recited, among others, in DePamphilis M L. (Cell Cycle. 2005 January; 4(1): 70-9).

Since preRC proteins act most "upstream" in the replication licensing cascade and given their prominent cell cycle regulatory role ORC in general and Orc-1 in particular are very promising targets when aiming at the control of cell proliferation via the DNA replication pathway. Insofar, any statement made herein related to ORC is, if not explicitly stated to the contrary, also applicable to Orc-1, and vice versa. The rationale behind this is that Orc-1 forms part of a complex which is referred to as ORC as shown in several publication (Ranjan and Gossen, PNAS 2006; 103:4864-9; Noguchi, K. et al. EMBO J. 2006, 25:5372-82; Vashee, S. et al. Genes Dev. 2003; 17:1894-908) As Orc-1 is an essential part of ORC, i.e. the complex, the lack of Orc-1 as caused by the down-regulation of Orc-1 by means of the nucleic acid molecules subject to the instant application, does not allow the formation of a functional ORC. A functional ORC is preferably one which is capable of initiating pre-RC formation on DNA (Ranjan and Gossen, PNAS 2006; 103:4864-9; Noguchi, K. et al. EMBO J. 2006, 25:5372-82; Vashee, S. et al. Genes Dev. 2003; 17:1894-908). Apart from being in principle an appropriate target for the treatment of cancer, Orc in general and Orc-1 in particular is furthermore a suitable target for the treatment of virus mediated diseases such as viral infections and viral diseases, particularly in case such viruses are double-stranded DNA viruses. Without wishing to be bound by any theory, the present inventors are of the opinion that the replication mechanism of viruses and of double-stranded DNA viruses in particular also makes use of Orc in general and Orc-1 in particular. In other words, Orc in general and Orc-1 in particular and the human replication initiation complex is required for the replication from a viral origin of replication. This has been shown, among others, in Dhar S K et al (Cell 106(3): 287-296 (2001)) for Epstein-Barr virus which is regarded as a model virus insofar. Another virus where this has been confirmed is Kaposi's sarcoma-associated herpesvirus (KSHV) Stedman et al (J Virol 78(22): 12566-12575 (2004)). It will be acknowledged by a person skilled in the art that such involvement of Orc is not limited to the Epstein-Barr virus. Rather a person skilled in the art may easily determine by routine experiments whether a virus involves Orc and more specifically Orc-1 in its replication. If Orc and more specifically Orc-1 are involved, the virus may be targeted by the compounds subject to the present application and the diseases associated with or caused by such virus may be treated by such compounds. Because of this involvement of Orc-1 in the replication of viruses and more specifically dsDNA viruses, any antagonist to Orc-1, including the nucleic acid molecules disclosed herein, are also suitable to inhibit viral replication and thus to treat any disease which is caused by or associated with viruses, more specifically replicating viruses involving Orc-1 in their replication.

Experiments for determining whether a virus involves ORC and more specifically Orc-1 when replicating are known to the person skilled in the art. Typically, such experiment involves a culture of cells in which the virus to be tested may, in principle, replicate. Such culture is exposed to the virus to be tested and to an antagonist of ORC and Orc-1 in particular, such antagonist may, among others, be one of the compounds according to the present invention. Other antagonists will be obvious to a person skilled in the art. In one embodiment, the cell culture is a conditional knock-down cell for ORC and Orc-1 in particular. This means that under defined conditions such as a distinct temperature, ORC and Orc-1 in particular is no longer active or no longer expressed which creates an experimental set-up comparable to the one where an antagonist of ORC and Orc-1 is used. The replication of the virus is determined prior and during or after the exposure of the virus infected cell line to the antagonist. Such determination of virus replication may be performed by any measure known to a person skilled in the art such as, including but not limited to, in situ hybridization, incorporation of radioactivity into the viral nucleic acid, changes in particle number, namely infectious units and the like. Such methods are, among others, described in Iwata S. et al (J Clin Virol 37(2): 128-33 (2006)).

Particularly preferred groups of viruses and diseases which can be treated by the compounds according to the present invention are all double-stranded DNA viruses and in particular EBV (Epstein-Barr-Virus), and Kaposi's sarcoma-associated herpesvirus and also papillomaviridae, particularly for the treatment of skin and genital warts, abnormal tissue changes (including cancer) of the vocal cords, mouth, hands, feet and genital organs, herpesviridae, particularly for the treatment of oral and genital herpes, chickenpox, particular for the treatment of Kaposi-associated herpes, poxviridae, particularly for the treatment of small pox.

The selectivity of the compounds according to the present invention in terms of affecting viral replication rather than the replication of the cell infected by said virus and thus the required specificity of the compounds of the present invention which is required so as to avoid undesired side-effects results form the increased sensitivity to lowering ORC levels of viral DNA replication compared to cellular DNA replication.

Without wishing to be bound by any theory, it seems that this characteristic arises from the little redundancy of viral genome and viral physiology which also holds true for silencing of the ORC function, where a virus with a single origin is much more sensitive than the host cell which can more easily compensate for inactivity of a subset of its multiple origins as underlying the findings of Dhar et al. Dhar S K et al (Cell 106(3): 287-296 (2001) (supra)

As outlined in more detail in the following, the subject matter of the instant application, in one aspect, is a nucleic acid molecule comprising a double-stranded structure, whereby the double-stranded structure comprises a first strand and a second strand, whereby the first strand comprises a first stretch of contiguous nucleotides and said first stretch is at least partially complementary to a target nucleic acid and whereby the second strand comprises a second stretch of contiguous nucleotides and said second stretch is at least partially complementary to the first stretch, whereby the target nucleic acid is the Orc-1 gene, more specifically the mRNA thereof.

In a preferred embodiment of the various aspects of the present invention the mRNA is a human mRNA of orc-1. In an even more preferred embodiment the target nucleic acid is an mRNA having a nucleic acid sequence in accordance with SEQ.ID.No.1. It is too acknowledged by the ones skilled in the art that there may be one or several single nucleotide changes in the mRNA in various individuals or groups of individuals, preferably in a population, compared to the mRNA having the nucleotide sequence of SEQ.ID.No. 1. Such mRNA having one or several single nucleotide changes compared to the mRNA having a nucleic acid sequence of SEQ.ID.No. 1 shall also be comprised by the term target nucleic acid as preferably used herein. In a still further embodiment the nucleic acid molecule according to the various aspects of the invention is suitable to inhibit the expression of Orc-1 and the mRNA coding thereof. More preferably such expression is inhibited by a mechanism which is referred to as RNA interference or post-transcriptional gene silencing. The siRNA molecule and RNAi molecule respectively, according to the present invention is thus suitable to trigger the RNA interference response resulting preferably in the knock-down of the mRNA for the target molecule. Insofar, this kind of nucleic acid molecule is suitable to decrease the expression of a target molecule by decreasing the expression at the level of mRNA. It will be acknowledged by the one skilled in the art that there may be further mRNAs coding for Orc-1 which shall also be encompassed by the present application. More specifically, the particular nucleotide positions identified herein by reference to SEQ.ID.NO. 1 can be identified in such further mRNAs by the one skilled in the art based on the technical teaching provided herein.

It is also to be acknowledged that the double-stranded nucleic acid according to this aspect of the present invention may have any of the designs described herein for this kind of nucleic acid molecule. It is furthermore to be acknowledged that the mechanism described above is, in a preferred embodiment also applicable to the nucleic acids disclosed herein in connection with the various aspects and design principles also referred to herein as sub-aspects.

RNA interference refers to the process of sequence specific post-transcriptional gene silencing in animals mediated by short interfering RNAs (siRNAs) (Fire et al., 1998, *Nature,* 391, 806). The corresponding process in plants is commonly referred to as post-transcriptional gene silencing or RNA silencing and is also referred to as quelling in fungi. The process of post-transcriptional gene silencing is thought to be an evolutionarily-conserved cellular defence mechanism used to prevent the expression of foreign genes which is commonly shared by diverse flora and phyla (Fire et al., 1999, *Trends Genet.,* 15, 358). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism which is also existing in animal cells and in particular also in mammalian cells, appears to be different from the interferon response that results from dsRNA-mediated activation of protein kinase PKR and 2',5'-oligoadenylate synthetase resulting in non-specific cleavage of mRNA by ribonuclease L.

The basic design of siRNA molecules or RNAi molecules, which mostly differ in the size, is basically such that the nucleic acid molecule comprises a double-stranded structure. The double-stranded structure comprises a first strand and a second strand. More preferably, the first strand comprises a first stretch of contiguous nucleotides and the second stretch comprises a second stretch of contiguous nucleotides. At least the first stretch and the second stretch are essentially complementary to each other. Such complementarity is typically based on Watson-Crick base pairing or other base-pairing mechanism known to the one skilled in the art, including but not limited to Hoogsteen base-pairing and others. It will be acknowledged by the one skilled in the art that depending on the length of such double-stranded structure a perfect match in terms of base complementarity is not necessarily required. However, such perfect complementarity is preferred in some embodiments. In a particularly preferred embodiment the complementarity and/or identity is at least 75%, 80%, 85%, 90% or 95%. In an alternative particularly preferred embodiment, the complementarity and/or identity is such that the complement and/or identical nucleic acid molecule hybridizes to one of the strands of the nucleic acid molecule according to the present invention, more preferably to one of the two stretches under the following conditions: It is capable of hybridizing with a portion of the target gene transcript under the following conditions: 400 mM NaCl, 40 mM PIPES pH 6.4, 1 mM EDTA, 50° C. or 70° C. hybridisation for 12-16 hours, followed by washing. Respective reactions conditions are, among others described in European patent EP 1 230 375. In any case, the nucleic acid molecules according to the present invention are designed or embodied such that they are suitable for gene silencing and more specifically suitable to trigger RNA interference.

A mismatch is also tolerable, mostly under the proviso that the double-stranded structure or any functional part thereof is still suitable to trigger the RNA interference mechanism, and that preferably such double-stranded structure is still stably forming under physiological conditions as prevailing in a cell, tissue and organism, respectively, containing or in principle containing such cell, tissue and organ. More preferably, the double-stranded structure is stable at 37° C. in a physiological buffer. It will be acknowledged by the ones skilled in the art that this kind of mismatch can preferably be contained at a position within the nucleic acid molecule according to the present invention different from the core region.

The features and conditions outlined above for the complementarity of the first strand and the second strand are also applicable with regard to the complementarity and identity respectively, of the first strand and first stretch, respectively, to the target nucleic acid, i.e. the nucleic acid coding for the target, and with regard to the complementarity and identity, respectively, of the second strand and second stretch, respectively, to the target nucleic acid, i.e. the nucleic acid coding for the target.

The first stretch is typically at least partially complementary to a target nucleic acid and the second stretch is, particularly given the relationship between the first and second stretch, respectively, in terms of base complementarity, at least partially identical to the target nucleic acid. The target nucleic acid is preferably an mRNA, although other forms of RNA such as hnRNAs are also suitable for the purpose of the nucleic acid molecule as disclosed herein.

Although RNA interference can be observed upon using long nucleic acid molecules comprising several dozens and sometimes even several hundreds of nucleotides and nucleotide pairs, respectively, shorter RNAi molecules are generally preferred. A more preferred range for the length of the first stretch and/or second stretch is from about 18 to 29 consecutive nucleotides, preferably 19 to 25 consecutive nucleotides and more preferably 19 to 23 consecutive nucleotides. More preferably, both the first stretch and the second stretch have the same length. In a further embodiment, the double-stranded structure comprises preferably between 16 and 29, preferably 18 to 25, more preferably 19 to 23 and most preferably 19 to 21 base pairs.

Although in accordance with the present invention, in principle, any part of the mRNA coding for Orc-1 can be used for the design of such siRNA molecule and RNAi molecule, respectively, the present inventors have surprisingly found that the sequence starting with nucleotide positions of the mRNA of SEQ.ID.NO. 1 coding for the human Orc-1 (databank entry NM_004153.2) and having the nucleotide sequence of SEQ.ID.No.1 are particularly suitable to be addressed by RNA interference mediating molecule, preferably for the designing of the antisense strand of the double-stranded RNA:

1763 such as in case of ORC1-1B;
1912 such as in case of ORC1-3B;
1913 such as in case of ORC1-4B; and
2556 such as in case of ORC1-7B.

More specifically, the present inventors have surprisingly found that although these sequences and starting points are particularly preferred target sequence for expression inhibition of Orc-1, there is a core of nucleotides in the vicinity of these sequences which is particularly effective insofar. This core is in one embodiment a sequence consisting of the about 9 to 11 nucleotides of the above specified nucleotide sequences, whereby such about 9 to 11 nucleotides are preferably contiguous nucleotides. It is also preferred that the siRNA molecule which addresses or targets such mRNA molecule and such (core) sequence, respectively, comprises a stretch of contiguous nucleotides which, on the antisense strand, is strictly complementary to such about 9 to 11 nucleotides, and, on the sense strand, is strictly identical to such about 9 to 11 nucleotides. Strictly complementary preferably means that all of the about 9 to 11 nucleotides are complementary in terms of the Watson-Crick base pairing rules. Strictly identical preferably means that all of the about 9 to 11 nucleotides are identical in terms of the individual nucleotide. Starting therefrom, the core can be extended such that a functionally active double-stranded nucleic acid molecule is obtained, whereby preferably functionally active means suitable to affect expression inhibition of Orc-1. For such purpose, the second stretch which is essentially identical to the corresponding part of the mRNA, i.e. the core sequence, is thus prolonged by one, preferably several nucleotides at the 5' end, whereby the thus added nucleotides are essentially identical to the nucleotides present in the target nucleic acid at the corresponding positions. Also for such purpose, the first strand which is essentially complementary to the target nucleic acid, is thus prolonged by one, preferably several nucleotides at the 3' end, whereby the thus added nucleotides are essentially complementary to the nucleotides present in the target nucleic acid at the corresponding positions, i.e. at the 5' end.

In accordance with this design principle, the core sequences of the antisense strand according to the present invention can be summarized as follows:

5' agaugucuu 3';

5' auugaaagg 3';

5' uauugaaag 3';
and

5' ucucaggaa 3'.

In a further embodiment thereof, the core sequence is identical to the nucleotide sequence of the second stretch of the double-stranded nucleic acid molecule according to the present invention and the first stretch essentially complementary thereto. In a still further preferred embodiment, the length of the double-stranded nucleic acid molecule according to the present invention is within the limits disclosed herein in connection with the various aspects and sub-aspects, respectively.

In the following preferred nucleic acid molecules according to the present invention are defined by their sequences.

In the following preferred nucleic acid molecules according to the present invention are defined by their sequences.
siRNA molecule ORC1-1 consisting of:

```
ORC1-1B
aggaauuccaagacaucua      (SEQ.ID.No: 2)

ORC1-1A
uagaugucuuggaauuccu      (SEQ.ID.No: 3)
```
or
siRNA molecule ORC1L-21-h-1 consisting of:

```
ORC1L-21-h-1B
acaggaauuccaagacaucua    (SEQ.ID.No: 22)

ORC1L-21-h-1A
uagaugucuuggaauuccugu    (SEQ.ID.No: 23)
``` siRNA molecule ORC1L-23-h-1 consisting of:

```
ORC1L-23-h-1B
gaacaggaauuccaagacaucua  (SEQ.ID.No: 24)

ORC1L-23-h-1A
uagaugucuuggaauuccuguuc  (SEQ.ID.No: 25)
``` siRNA molecule ORC1L-25-h-1 consisting of:

```
ORC1L-25-h-1B
gggaacaggaauuccaagacaucua  (SEQ.ID.No: 26)

ORC1L-25-h-1A
uagaugucuuggaauuccuguuccc  (SEQ.ID.No: 27)
``` which differ from ORC1-1 by the addition of 2, 4 and 6 nucleotides, respectively.

siRNA molecule ORC1-2 consisting of:

```
ORC1-2B
gucccugggacagggaaga      (SEQ.ID.No: 4)

ORC1-2A
ucuucccugucccagggac      (SEQ.ID.No: 5)
``` or
siRNA molecule ORC1L-21-h-2 consisting of:

```
ORC1L-21-h-2B
gugucccugggacagggaaga    (SEQ.ID.No: 28)

ORC1L-21-h-2A
ucuucccugucccagggacac    (SEQ.ID.No: 29)
``` siRNA molecule ORC1L-23-h-2 consisting of:

```
ORC1L-23-h-2B
cggugucccugggacagggaaga  (SEQ.ID.No: 30)

ORC1L-23-h-2A
ucuucccugucccagggacaccg  (SEQ.ID.No: 31)
``` siRNA molecule ORC1L-25-h-2 consisting of:

```
ORC1L-25-h-2B
uccggugucccugggacagggaaga   (SEQ.ID.No: 32)

ORC1L-25-h-2A
ucuucccugucccagggacaccgga   (SEQ.ID.No: 33)
``` which differ from ORC1-2 by the addition of 2, 4 and 6 nucleotides, respectively.
siRNA molecule ORC1-3 consisting of

```
ORC1-3B
gauguuccucccuuucaau      (SEQ.ID.No: 6)

ORC1-3A
auugaaagggaggaacauc      (SEQ.ID.No: 7)
``` or
siRNA molecule ORC1L-21-h-3 consisting of:

```
ORC1L-21-h-3B
augauguuccucccuuucaau    (SEQ.ID.No: 34)

ORC1L-21-h-3A
auugaaagggaggaacaucau    (SEQ.ID.No: 35)
``` siRNA molecule ORC1L-23-h-3 consisting of:

```
ORC1L-23-h-3B
caaugauguuccucccuuucaau  (SEQ.ID.No: 20)

ORC1L-23-h-3A
auugaaagggaggaacaucauug  (SEQ.ID.No: 21)
``` siRNA molecule ORC1L-25-h-3 consisting of:

```
ORC1L-25-h-3B
gccaaugauguuccucccuuucaau   (SEQ.ID.No: 36)

ORC1L-25-h-3A
auugaaagggaggaacaucauuggc   (SEQ.ID.No: 37)
``` which differ from ORC1-3 by the addition of 2, 4 and 6 nucleotides, respectively.

siRNA molecule ORC1-4 consisting of:

```
ORC1-4B
auguuccucccuuucaaua      (SEQ.ID.No: 8)

ORC1-4A
uauugaaagggaggaacau      (SEQ.ID.No: 9)
``` or
siRNA molecule ORC1L-21-h-4 consisting of:

```
ORC1L-21-h-4B
ugauguuccucccuuucaaua    (SEQ.ID.No: 38)

ORC1L-21-h-4A
uauugaaagggaggaacauca    (SEQ.ID.No: 39)
``` siRNA molecule ORC1L-23-h-4 consisting of

```
ORC1L-23-h-4B
aaugauguuccucccuuucaaua  (SEQ.ID.No: 40)

ORC1L-23-h-4A
uauugaaagggaggaacaucauu  (SEQ.ID.No: 41)
``` siRNA molecule ORC I L-25-h-4 consisting of:

```
ORC1L-25-h-4B
ccaaugauguuccucccuuucaaua   (SEQ.ID.No: 42)

ORC1L-25-h-4A
uauugaaagggaggaacaucauugg   (SEQ.ID.No: 43)
``` which differ from ORC1-4 by the addition of 2, 4 and 6 nucleotides, respectively.
siRNA molecule ORC1-5 consisting of

```
ORC1-5B
cccaccaagucuaugugca      (SEQ.ID.No: 10)

ORC1-5A
ugcacauagacuugguggg      (SEQ.ID.No: 11)
``` or
siRNA molecule ORC1L-21-h-5 consisting of

```
ORC1L-21-h-5B
gccccaccaagucuaugugca    (SEQ.ID.No: 44)

ORC1L-21-h-5A
ugcacauagacuuggugggc     (SEQ.ID.No: 45)
``` siRNA molecule ORC1L-23-h-5 consisting of:

```
ORC1L-23-h-5B
gagccccaccaagucuaugugca  (SEQ.ID.No: 46)

ORC1L-23-h-5A
ugcacauagacuuggugggcuc   (SEQ.ID.No: 47)
``` siRNA molecule ORC1L-25-h-5 consisting of:

```
ORC1L-25-h-5B
cggagccccaccaagucuaugugca   (SEQ.ID.No: 48)

ORC1L-25-h-5A
ugcacauagacuuggugggcuccg    (SEQ.ID.No: 49)
``` which differ from ORC1-5 by the addition of 2, 4 and 6 nucleotides, respectively.

siRNA molecule ORC1-6 consisting of:

```
ORC1-6B
uguggacucacaaacaaga        (SEQ.ID.No: 12)

ORC1-6A
ucuuguuugugaguccaca        (SEQ.ID.No: 13)
``` or
siRNA molecule ORC1L-21-h-6 consisting of:

```
ORC1L-21-h-6B
ucuguggacucacaaacaaga      (SEQ.ID.No: 50)

ORC1L-21-h-6A
ucuuguuugugaguccacaga      (SEQ.ID.No: 51)
``` siRNA molecule ORC1L-23-h-6 consisting of:

```
ORC1L-23-h-6B
cuucuguggacucacaaacaaga    (SEQ.ID.No: 52)

ORC1L-23-h-6A
ucuuguuugugaguccacagaag    (SEQ.ID.No: 53)
``` siRNA molecule ORC1L-25-h-6 consisting of:

```
ORC1L-25-h-6B
accuucuguggacucacaaacaaga  (SEQ.ID.No: 54)

ORC1L-25-h-6A
ucuuguuugugaguccacagaaggu  (SEQ.ID.No: 55)
``` which differ from ORC1-2 by the addition of 2, 4 and 6 nucleotides, respectively.
siRNA molecule ORC1-7 consisting of:

```
ORC1-7B
ggaacagagcuuccugaga        (SEQ.ID.No: 14)

ORC1-7A
ucucaggaagcucuguucc        (SEQ.ID.No: 15)
``` or
siRNA molecule ORC1L-21-h-7 consisting of:

```
ORC1L-21-h-7B
cuggaacagagcuuccugaga      (SEQ.ID.No: 56)

ORC1L-21-h-7A
ucucaggaagcucuguuccag      (SEQ.ID.No: 57)
``` siRNA molecule ORC1L-23-h-7 consisting of:

```
ORC1L-23-h-7B
uucuggaacagagcuuccugaga    (SEQ.ID.No: 58)

ORC1L-23-h-7A
ucucaggaagcucuguuccagaa    (SEQ.ID.No: 59)
``` siRNA molecule ORC1L-25-h-7 consisting of:

```
ORC1L-25-h-7B
uguucuggaacagagcuuccugaga  (SEQ.ID.No: 60)

ORC1L-25-h-7A
ucucaggaagcucuguuccagaaca  (SEQ.ID.No: 61)
``` which differ from ORC1-7 by the addition of 2, 4 and 6 nucleotides, respectively.

siRNA molecule ORC1-8 consisting of:

```
ORC1-8B
ccacguuucaacagauaua        (SEQ.ID.No: 16)

ORC1-8A
uauaucuguugaaacgugg        (SEQ.ID.No: 17)
``` or
siRNA molecule ORC1L-21-h-8 consisting of:

```
ORC1L-21-h-8B
agccacguuucaacagauaua      (SEQ.ID.No: 62)

ORC1L-21-h-8A
uauaucuguugaaacguggcu      (SEQ.ID.No: 63)
``` siRNA molecule ORC1L-23-h-8 consisting of

```
ORC1L-23-h-8B
gaagccacguuucaacagauaua    (SEQ.ID.No: 64)

ORC1L-23-h-8A
uauaucuguugaaacguggcuuc    (SEQ.ID.No: 65)
``` siRNA molecule ORC1L-25-h-8 consisting of:

```
ORC1L-25-h-8B
aggaagccacguuucaacagauaua  (SEQ.ID.No: 66)

ORC1L-25-h-8A
uauaucuguugaaacguggcuuccu  (SEQ.ID.No: 67)
``` which differ from ORC1-8 by the addition of 2, 4 and 6 nucleotides, respectively.

Preferred nucleic acid molecules according to the present invention are siRNA molecules ORC1-1, ORC1L-21-h-1, ORC1L-23-h-1, ORC1L-25-h-1; ORC1-3, ORC1L-21-h-3, ORC1L-23-h-3, ORC1L-25-h-3; ORC1-4, ORC1L-21-h-4, ORC1L-23-h-4, ORC1L-25-h-4; ORC1-7, ORC1L-21-h-7, ORC1L-23-h-7, ORC1L-25-h-7, and ORC1L-25-h-7.

In a preferred embodiment the above defined nucleic acid molecules according to the present invention are modified as follows, whereby it is to be acknowledged that the sequence of the respective nucleic acid molecules remains the same:
siRNA molecule ORC1-1 consisting of:

```
ORC1-1B
aggaauuccaagacaucua        (SEQ.ID.No: 2)

ORC1-1A
uagaugucuuggaauuccu        (SEQ.ID.No: 3)
``` or
siRNA molecule ORC1L-21-h-1 consisting of:

```
ORC1L-21-h-1B
acaggaauuccaagacaucua      (SEQ.ID.No: 22)

ORC1L-21-h-1A
uagaugucuuggaauuccugu      (SEQ.ID.No: 23)
``` siRNA molecule ORC1L-23-h-1 consisting of:

```
ORC1L-23-h-1B
gaacaggaauuccaagacaucua    (SEQ.ID.No: 24)

ORC1L-23-h-1A
uagaugucuuggaauuccuguuc    (SEQ.ID.No: 25)
``` siRNA molecule ORC1L-25-h-1 consisting of:

```
ORC1L-25-h-1B
gggaacaggaauuccaagacaucua    (SEQ.ID.No: 26)

ORC1L-25-h-1A
uagaugucuuggaauuccuguuccc    (SEQ.ID.No: 27)
``` which differ from ORC1-1 by the addition of 2, 4 and 6 nucleotides, respectively.

siRNA molecule ORC1-2 consisting of:

```
ORC1-2B
gucccugggacagggaaga    (SEQ.ID.No: 4)

ORC1-2A
ucuuccugucccagggac     (SEQ.ID.No: 5)
``` or
siRNA molecule ORC1L-21-h-2 consisting of:

```
ORC1L-21-h-2B
gugucccugggacagggaaga    (SEQ.ID.No: 28)

ORC1L-21-h-2A
ucuuccugucccagggacac     (SEQ.ID.No: 29)
``` siRNA molecule ORC1L-23-h-2 consisting of:

```
ORC1L-23-h-2B
cggugucccugggacagggaaga    (SEQ.ID.No: 30)

ORC1L-23-h-2A
ucuuccugucccagggacaccg     (SEQ.ID.No: 31)
``` siRNA molecule ORC1L-25-h-2 consisting of:

```
ORC1L-25-h-2B
uccggugucccugggacagggaaga   (SEQ.ID.No: 32)

ORC1L-25-h-2A
ucuuccugucccagggacaccgga    (SEQ.ID.No: 33)
``` which differ from ORC1-2 by the addition of 2, 4 and 6 nucleotides, respectively.

siRNA molecule ORC1-3 consisting of:

```
ORC1-3B
gauguuccucccuuucaau    (SEQ.ID.No: 6)

ORC1-3A
auugaagggaggaacauc     (SEQ.ID.No: 7)
``` or
siRNA molecule ORC IL-21-h-3 consisting of:

```
ORC1L-21-h-3B
augauguuccucccuuucaau    (SEQ.ID.No: 34)

ORC1L-21-h-3A
auugaaagggaggaacaucau    (SEQ.ID.No: 35)
``` siRNA molecule ORC1L-23-h-3 consisting of:

```
ORC1L-23-h-3B
caaugauguuccucccuuucaau    (SEQ.ID.No: 20)

ORC1L-23-h-3A
auugaaagggaggaacaucauug    (SEQ.ID.No: 21)
``` siRNA molecule ORC1L-25-h-3 consisting of

```
ORC1L-25-h-3B
gccaaugauguuccucccuuucaau    (SEQ.ID.No: 36)

ORC1L-25-h-3A
auugaaagggaggaacaucauuggc    (SEQ.ID.No: 37)
``` which differ from ORC1-3 by the addition of 2, 4 and 6 nucleotides, respectively.

siRNA molecule ORC1-4 consisting of:

```
ORC1-4B
auguuccucccuuucaaua    (SEQ.ID.No: 8)

ORC1-4A
uauugaaagggaggaacau    (SEQ.ID.No: 9)
``` or
siRNA molecule ORC1L-21-h-4 consisting of:

```
ORC1L-21-h-4B
ugauguuccucccuuucaaua    (SEQ.ID.No: 38)

ORC1L-21-h-4A
uauugaaagggaggaacauca    (SEQ.ID.No: 39)
``` siRNA molecule ORC1L-23-h-4 consisting of:

```
ORC1L-23-h-4B
aaugauguuccucccuuucaaua    (SEQ.ID.No: 40)

ORC1L-23-h-4A
uauugaaagggaggaacaucauu    (SEQ.ID.No: 41)
``` siRNA molecule ORC1L-25-h-4 consisting of:

```
ORC1L-25-h-4B
ccaaugauguuccucccuuucaaua    (SEQ.ID.No: 42)

ORC1L-25-h-4A
uauugaaagggaggaacaucauugg    (SEQ.ID.No: 43)
``` which differ from ORC1-4 by the addition of 2, 4 and 6 nucleotides, respectively.

siRNA molecule ORC1-5 consisting of:

```
ORC1-5B
cccaccaagucuaugugca    (SEQ.ID.No: 10)

ORC1-5A
ugcacauagacuuggugggg    (SEQ.ID.No: 11)
``` or
siRNA molecule ORC1L-21-h-5 consisting of:

```
ORC1L-21-h-5B
gccccaccaagucuaugugca    (SEQ.ID.No: 44)

ORC1L-21-h-5A
ugcacauagacuuggugggc     (SEQ.ID.No: 45)
``` siRNA molecule ORC1L-23-h-5 consisting of:

```
ORC1L-23-h-5B
gagccccaccaagucuaugugca    (SEQ.ID.No: 46)

ORC1L-23-h-5A
ugcacauagacuuggugggcuc     (SEQ.ID.No: 47)
``` siRNA molecule ORC1L-25-h-5 consisting of:

```
ORC1L-25-h-5B
cggagcccaccaagucuaugugca      (SEQ.ID.No: 48)

ORC1L-25-h-5A
ugcacauagacuuggugggguccg      (SEQ.ID.No: 49)
``` which differ from ORC1-5 by the addition of 2, 4 and 6 nucleotides, respectively.

siRNA molecule ORC1-6 consisting of:

```
ORC1-6B
uguggacucacaaacaaga           (SEQ.ID.No: 12)

ORC1-6A
ucuuguuugugaguccaca           (SEQ.ID.No: 13)
``` or
siRNA molecule ORC1L-21-h-6 consisting of:

```
ORC1L-21-h-6B
ucuguggacucacaaacaaga         (SEQ.ID.No: 50)

ORC1L-21-h-6A
ucuuguuugugaguccacaga         (SEQ.ID.No: 51)
``` siRNA molecule ORC1L-23-h-6 consisting of:

```
ORC1L-23-h-6B
cuucuguggacucacaaacaaga       (SEQ.ID.No: 52)

ORC1L-23-h-6A
ucuuguuugugaguccacagaag       (SEQ.ID.No: 53)
``` siRNA molecule ORC1L-25-h-6 consisting of:

```
ORC1L-25-h-6B
accuucuguggacucacaaacaaga     (SEQ.ID.No: 54)

ORC1L-25-h-6A
ucuuguuugugaguccacagaaggu     (SEQ.ID.No: 55)
``` which differ from ORC1-2 by the addition of 2, 4 and 6 nucleotides, respectively.

siRNA molecule ORC1-7 consisting of:

```
ORC1-7B
ggaacagagcuuccugaga           (SEQ.ID.No: 14)

ORC1-7A
ucucaggaagcucuguucc           (SEQ.ID.No: 15)
``` or
siRNA molecule ORC1L-21-h-7 consisting of:

```
ORC1L-21-h-7B
cuggaacagagcuuccugaga         (SEQ.ID.No: 56)

ORC1L-21-h-7A
ucucaggaagcucuguuccag         (SEQ.ID.No: 57)
``` siRNA molecule ORC1L-23-h-7 consisting of:

```
ORC1L-23-h-7B
uucuggaacagagcuuccugaga       (SEQ.ID.No: 58)

ORC1L-23-h-7A
ucucaggaagcucuguuccagaa       (SEQ.ID.No: 59)
``` siRNA molecule ORC1L-25-h-7 consisting of:

```
ORC1L-25-h-7B
uguucuggaacagagcuuccugaga     (SEQ.ID.No: 60)

ORC1L-25-h-7A
ucucaggaagcucuguuccagaaca     (SEQ.ID.No: 61)
``` which differ from ORC1-7 by the addition of 2, 4 and 6 nucleotides, respectively.

siRNA molecule ORC1-8 consisting of:

```
ORC1-8B
ccacguuucaacagauaua           (SEQ.ID.No: 16)

ORC1-8A
uauaucguugaaacgugg            (SEQ.ID.No: 17)
``` or
siRNA molecule ORC1L-21-h-8 consisting of:

```
ORC1L-21-h-8B
agccacguuucaacagauaua         (SEQ.ID.No: 62)

ORC1L-21-h-8A
uauaucuguugaaacguggcu         (SEQ.ID.No: 63)
``` siRNA molecule ORC1L-23-h-8 consisting of:

```
ORC1L-23-h-8B
gaagccacguuucaacagauaua       (SEQ.ID.No: 64)

ORC1L-23-h-8A
uauaucuguugaaacguggcuuc       (SEQ.ID.No: 65)
``` siRNA molecule ORC1L-25-h-8 consisting of:

```
ORC1L-25-h-8B
aggaagccacguuucaacagauaua     (SEQ.ID.No: 66)

ORC1L-25-h-8A
uauaucuguugaaacguggcuuccu     (SEQ.ID.No: 67)
``` which differ from ORC1-8 by the addition of 2, 4 and 6 nucleotides, respectively.

Preferred nucleic acid molecules according to the present invention are siRNA molecules ORC1-1, ORC1L-21-h-1, ORC1L-23-h-1, ORC1L-25-h-1; ORC1-3, ORC1L-21-h-3, ORC1L-23-h-3, ORC1L-25-h-3; ORC1-4, ORC1L-21-h-4, ORC1L-23-h-4, ORC1L-25-h-4; ORC1-7, ORC1L-21-h-7, ORC1L-23-h-7, ORC1L-25-h-7, and ORC1L-25-h-7 having the modification as outlined above.

Any underlined and bold printed nucleotide in the above Table is modified at the 2' position such as to be 2'-O-methyl; non-underlined nucleotides are non-modified nucleotides having a OH group at the 2' position.

It is to be acknowledged that A stands for the antisense strand which is also referred to herein as the first strand; B stands for the sense strand which is also referred to herein as the second strand. Please note that any sequence indicated in the instant application is presented in 5'→3' direction, if not explicitly indicated to the contrary.

It will be acknowledged by the ones skilled in the art that the particular design of the siRNA molecules and the RNAi molecules, respectively, can vary in accordance with the current and future design principles, whereby in preferred embodiments the sequences of such siRNA molecules and RNAi molecules, respectively, consist of or comprise one or both of the sequences outlined above. For the time being some design principles exist which shall be discussed in more detail in the following and which shall be referred to as sub-aspects or sub-aspects of the first aspect of the nucleic acid molecule according to the present invention. It is within the present invention that all features and embodiments described for one particular sub-aspect, i.e. design of the nucleic acid, are also applicable to any other aspect and sub-aspect of the nucleic acid according to the present invention and thus form respective embodiments thereof.

The first sub-aspect is related to nucleic acid according to the present invention, whereby the first stretch comprises a plurality of groups of modified nucleotides having a modification at the 2' position, whereby within the stretch each group of modified nucleotides is flanked on one or both sides by a flanking group of nucleotides, whereby the flanking nucleotide(s) forming the flanking group(s) of nucleotides is either an unmodified nucleotide or a nucleotide having a modification different from the modification of the modified nucleotides. Such design is, among others described in international patent application WO 2004/015107. The nucleic acid according to this aspect is preferably a ribonucleic acid although, as will be outlined in some embodiments, the modification at the 2' position results in a nucleotide which as such is, from a pure chemical point of view, no longer a ribonucleotide. However, it is within the present invention that such modified ribonucleotide shall be regarded and addressed herein as a ribonucleotide and the molecule containing such modified ribonucleotide as a ribonucleic acid.

In an embodiment of the ribonucleic acid according to the first sub-aspect of the present invention the ribonucleic acid is blunt ended, either on one side or on both sides of the double-stranded structure. In a more preferred embodiment the double-stranded structure comprises 18 to 25, more preferably 19 to 23 and, alternatively, 18 or 19 base pairs. In an even more preferred embodiment, the nucleic acid consists of the first stretch and the second stretch only.

In a further embodiment of the ribonucleic acid according to the first sub-aspect of the present invention said first stretch and/or said second stretch comprise a plurality of groups of modified nucleotides. In a further preferred embodiment the first stretch also comprises a plurality of flanking groups of nucleotides. In a preferred embodiment a plurality of groups means at least two groups.

In another embodiment of the ribonucleic acid according to the first sub-aspect of the present invention said second stretch comprises a plurality of groups of modified nucleotides. In a further preferred embodiment the second stretch also comprises a plurality of flanking groups of nucleotides. In a preferred embodiment a plurality of groups means at least two groups.

In a further preferred embodiment both the first and the second stretch comprise a plurality of both groups of modified nucleotides and flanking groups of nucleotides. In a more preferred embodiment the plurality of both groups of modified nucleotides and flanking groups of nucleotides form a pattern, preferably a regular pattern, on either the first stretch and/or the second stretch, whereby it is even more preferred that such pattern is formed on both the first and the second stretch. In a preferred embodiment such pattern is a spatial or positional pattern. A spatial or positional pattern as subject to this first sub-aspect means that (a) nucleotide(s) is/are modified dependent on the position within the nucleotide sequence of a strand/stretch forming the double-stranded structure. Accordingly, it does not matter whether the nucleotide to be modified is a pyrimidine or a purine. Rather the relative position of such nucleotide(s) relative to (a) non-modified nucleotide(s) and thus relative to the 5' end and the 3' end, respectively, is decisive insofar. Therefore, the modification(s) seen along the individual strand/stretch is thus not dependent on or even driven by the chemical nature of the individual nucleotide along such strand/stretch, but depends on the position of the individual nucleotide. Therefore, according to the technical teaching of this first sub-aspect of the present invention, the modification pattern will always be the same, irrespective of the sequence which is to be modified.

In a preferred embodiment of the ribonucleic acid according to the first sub-aspect of the present invention the group of modified nucleotides and/or the group of flanking nucleotides comprises a number of nucleotides whereby the number is selected from the group comprising one nucleotide to 10 nucleotides. In connection with any ranges specified herein it is to be understood that each range discloses any individual integer between the respective figures used to define the range including said two figures defining said range. In the present case the group thus comprises one nucleotide, two nucleotides, three nucleotides, four nucleotides, five nucleotides, six nucleotides, seven nucleotides, eight nucleotides, nine nucleotides and ten nucleotides.

In another embodiment of the ribonucleic acid according to the first sub-aspect of the present invention the pattern of modified nucleotides of said first stretch is the same as the pattern of modified nucleotides of said second stretch.

In a preferred embodiment of the ribonucleic acid according to the first sub-aspect of the present invention the pattern of said first stretch aligns with the pattern of said second stretch.

In an alternative embodiment of the ribonucleic acid according to the first sub-aspect of the present invention the pattern of said first stretch is shifted by one or more nucleotides relative to the pattern of the second stretch.

In an embodiment of the ribonucleic acid according to the first sub-aspect of the present invention the modification at the 2' position is selected from the group comprising amino, fluoro, methoxy, alkoxy and alkyl.

In another embodiment of the ribonucleic acid according to the first sub-aspect of the present invention the double stranded structure is blunt ended.

In a preferred embodiment of the ribonucleic acid according to the first sub-aspect of the present invention the double stranded structure is blunt ended on both sides of the double-stranded structure.

In another embodiment of the ribonucleic acid according to the first sub-aspect of the present invention the double stranded structure is blunt ended on the double stranded structure's side which is defined by the 5'-end of the first strand and the 3'-end of the second strand.

In still another embodiment of the ribonucleic acid according to the first sub-aspect of the present invention the double stranded structure is blunt ended on the double stranded structure's side which is defined by at the 3'-end of the first strand and the 5'-end of the second strand.

In another embodiment of the ribonucleic acid according to the first sub-aspect of the present invention at least one of the two strands has an overhang of at least one nucleotide at the 5'-end.

In a preferred embodiment of the ribonucleic acid according to the first sub-aspect of the present invention the overhang consists of at least one deoxyribonucleotide.

In a further embodiment of the ribonucleic acid according to the first sub-aspect of the present invention at least one of the strands has an overhang of at least one nucleotide at the 3'-end.

In an embodiment of the ribonucleic acid of the first sub-aspect the length of the double-stranded structure is from about 17 to 25, and more preferably 19 to 23 base pairs or 18 or 19 base pairs.

In another embodiment of the ribonucleic acid of the first sub-aspect the length of said first strand and/or the length of said second strand is independently from each other selected from the group comprising the ranges of from about 15 to about 23 base pairs, 19 to 23 base pairs and 18 or 19 base pairs.

In a preferred embodiment of the ribonucleic acid according to the first sub-aspect the present invention the complementarity between said first strand and the target nucleic acid is perfect.

In an embodiment of the ribonucleic acid according to the first sub-aspect the duplex formed between the first strand and the target nucleic acid comprises at least 15 nucleotides wherein there is one mismatch or two mismatches between said first strand and the target nucleic acid forming said double-stranded structure.

In an embodiment of the ribonucleic acid according to the first sub-aspect both the first strand and the second strand each comprise at least one group of modified nucleotides and at least one flanking group of nucleotides, whereby each group of modified nucleotides comprises at least one nucleotide and whereby each flanking group of nucleotides comprising at least one nucleotide with each group of modified nucleotides of the first strand being aligned with a flanking group of nucleotides on the second strand, whereby the most terminal 5' nucleotide of the first strand is a nucleotide of the group of modified nucleotides, and the most terminal 3' nucleotide of the second strand is a nucleotide of the flanking group of nucleotides. In a preferred embodiment, the first strand and the second strand each comprise at least two groups of modified nucleotides and at least two groups of flanking groups of nucleotides. In a still more preferred embodiment each and any individual group consists of a single nucleotide.

In a preferred embodiment of the ribonucleic acid according to of the first sub-aspect, each group of modified nucleotides consists of a single nucleotide and/or each flanking group of nucleotides consists of a single nucleotide.

In a further embodiment of the ribonucleic acid according to of the first sub-aspect, on the first strand the nucleotide forming the flanking group of nucleotides is an unmodified nucleotide which is arranged in a 3' direction relative to the nucleotide forming the group of modified nucleotides, and wherein on the second strand the nucleotide forming the group of modified nucleotides is a modified nucleotide which is arranged in 5' direction relative to the nucleotide forming the flanking group of nucleotides.

In another embodiment of the ribonucleic acid according to the first sub-aspect, the first strand comprises eight to twelve, preferably nine to eleven, groups of modified nucleotides, and wherein the second strand comprises seven to eleven, preferably eight to ten, groups of modified nucleotides.

It is within the present invention that what has been specified above is also applicable to the first and second stretch, respectively. This is particular true for those embodiments where the strand consists of the stretch only.

Taken the stretch of contiguous nucleotides a pattern of modification of the nucleotides forming the stretch may be realised in an embodiment such that a single nucleotide or group of nucleotides which are covalently linked to each other via standard phosphorodiester bonds or, at least partially, through phosphorothioate bonds, show such kind of modification. In case such nucleotide or group of nucleotides which is also referred to herein as group of modified nucleotides, is not forming the 5'-end or 3'-end of said stretch a nucleotide or group of nucleotides follows on both sides of the nucleotide which does not have the modification of the preceding nucleotide or group of nucleotides. It is to be noted that this kind of nucleotide or group of nucleotides, however, may have a different modification. This kind of nucleotide or group of nucleotides is also referred to herein as the flanking group of nucleotides. This sequence consisting of modified nucleotide and group(s) of modified nucleotides, respectively, and of unmodified or differently modified nucleotide or group(s) of unmodified or differently modified nucleotides may be repeated one or several times. Preferably, the sequence is repeated more than one time. For reason of clarity the pattern is discussed in more detail in the following, generally referring to a group of modified nucleotides or a group of unmodified nucleotides whereby each of said groups may actually comprise as little as a single nucleotide. Unmodified nucleotide as used herein means either not having any of the afore-mentioned modifications at the nucleotide forming the respective nucleotide or group of nucleotides, or having a modification which is different from the one of the modified nucleotide and group of nucleotides, respectively.

It is also within the present invention that the modification of the unmodified nucleotide(s) wherein such unmodified nucleotide(s) is/are actually modified in a way different from the modification of the modified nucleotide(s), can be the same or even different for the various nucleotides forming said unmodified nucleotides or for the various flanking groups of nucleotides.

The pattern of modified and unmodified nucleotides may be such that the 5'-terminal nucleotide of the strand or of the stretch starts with a modified group of nucleotides or starts with an unmodified group of nucleotides. However, in an alternative embodiment it is also possible that the 5'-terminal nucleotide is formed by an unmodified group of nucleotides.

This kind of pattern may be realised either on the first stretch or the second stretch of the interfering RNA or on both. This applies equally to the first strand and the second strand, respectively. It has to be noted that a 5' phosphate on the target-complementary strand of the siRNA duplex is required for siRNA function, suggesting that cells check the authenticity of siRNAs through a free 5' OH (which can be phosphorylated) and allow only such bona fide siRNAs to direct target RNA destruction (Nykanen, Cell 2001, 107, 309-321).

Preferably, the first stretch shows a kind of pattern of modified and unmodified groups of nucleotides, i.e. of group(s) of modified nucleotides and flanking groups) of nucleotides, whereas the second stretch does not show this kind of pattern. This may be useful insofar as the first stretch is actually the more important one for the target-specific degradation process underlying the interference phenomenon of RNA so that for specificity reasons the second stretch can be chemically modified so it is not functional in mediating RNA interference. This applies equally to the first strand and the second strand, respectively.

However, it is also within the present invention that both the first stretch and the second stretch have this kind of pattern. Preferably, the pattern of modification and non-modification is the same for both the first stretch and the second stretch. This applies equally to the first strand and the second strand, respectively.

In a preferred embodiment the group of nucleotides forming the second stretch and corresponding to the modified group of nucleotides of the first stretch are also modified whereas the unmodified group of nucleotides of or forming the second stretch correspond to the unmodified group of nucleotides of or forming the first stretch. Another alternative is that there is a phase shift of the pattern of modification of the first stretch and first strand, respectively, relative to the pattern of modification of the second stretch and second strand, respectively. Preferably, the shift is such that the modified group of nucleotides of the first stretch corresponds to the unmodified group of nucleotides of the second stretch and vice versa. As used in connection therewith the term "corresponds" preferably means that in a double-strand arrangement of said two strands and stretches, respectively, the nucleotide(s) of modified group of nucleotides is/are facing the nucleotide(s) of the unmodified group of nucleotides. It is also within the present invention that the phase shift of the pattern of modification is not complete but overlapping. This applies equally to the first strand and the second strand, respectively.

In a preferred embodiment the second nucleotide at the terminus of the strand and stretch, respectively, is an unmodified nucleotide or the beginning of group of unmodified nucleotides. Preferably, this unmodified nucleotide or unmodified group of nucleotides is located at the 5'-end of the first and second strand, respectively, and even more preferably of the first strand. In a further preferred embodiment the unmodified nucleotide or unmodified group of nucleotide is located at the 5'-end of the first strand and first stretch, respectively. In a preferred embodiment the pattern consists of alternating single modified and unmodified nucleotides.

In a further preferred embodiment of this aspect of the present invention the interfering ribonucleic acid subject comprises two strands, whereby a 2'-O-methyl modified nucleotide and a non-modified nucleotide, preferably a nucleotide which is not 2'-O-methyl modified, are incorporated on both strands in an alternate manner which means that every second nucleotide is a 2'-O-methyl modified and a non-modified nucleotide, respectively. This means that on the first strand one 2'-O-methyl modified nucleotide is followed by a non-modified nucleotide which in turn is followed by 2'-O-methyl modified nucleotide and so on. The same sequence of 2'-O-methyl modification and non-modification exists on the second strand, whereby there is preferably a phase shift such that the 2'-O-methyl modified nucleotide on the first strand base pairs with a non-modified nucleotide(s) on the second strand and vice versa. This particular arrangement, i.e. base pairing of 2'-O-methyl modified and non-modified nucleotide(s) on both strands is particularly preferred in case of short interfering ribonucleic acids, i.e. short base paired double-stranded ribonucleic acids because it is assumed, although the present inventors do not wish to be bound by that theory, that a certain repulsion exists between two base-pairing 2'-O-methyl modified nucleotides which would destabilise such duplex, and short duplexes in particular. About the particular arrangement, it is preferred if the antisense strand starts with a 2'-O-methyl modified nucleotide at the 5' end whereby consequently the second nucleotide is non-modified, the third, fifth, seventh and so on nucleotides are thus again 2'-O-methyl modified whereas the second, fourth, sixth, eighth and the like nucleotides are non-modified nucleotides. Again, not wishing to be bound by any theory, it seems that particular importance may be ascribed to the second, and optionally fourth, sixth, eighth and/or similar position(s) at the 5' terminal end of the antisense strand which should not comprise any modification, whereas the most 5' terminal nucleotide, i.e. the first 5' terminal nucleotide of the antisense strand may exhibit such modification with any uneven positions such as first, optionally third, fifth and similar position(s) at or of the antisense strand may be modified. In further embodiments the modification and non-modification, respectively, of the modified and non-modified nucleotide(s), respectively, may be anyone as described herein. In a more specific embodiment, the double-stranded nucleic acid molecule according to the present invention consists of a first strand of 19 to 23 consecutive nucleotides and a second strand of 19 to 23 consecutive nucleotides, whereby the first strand and the second strand are essentially complementary to each other and more preferably have the same length. Furthermore, in said more specific embodiment the double-stranded structure is blunt-ended at both end. The first strand which is essentially complementary to the target nucleic acid, i.e. an mRNA coding for Orc-1, starts at the 5' end with a nucleotide which is methylated at the 2'OH group forming a 2'O—Me group. Every second nucleotide of this first strand has the same modification, i.e. is methylated at the 2' OH group. Thus, the first, third, fifth and so on, i.e. any uneven nucleotide position of the first strand is modified in such a way. The nucleotides at the even positions of the first strand are either non-modified nucleotides or modified nucleotides, whereby if modified, the modification is different from the modification of the nucleotides at the uneven nucleotide positions of the first strand. The second strand preferably comprising the same number of nucleotides as the first strand, has a modified nucleotide at the second, fourth, sixth and so on, i.e. at any even nucleotide position when counting in contrast to the usual counting direction herein, which is 5'→3', from or in 3'→5' direction. Any of the other nucleotides, i.e. those at the uneven nucleotide positions are non-modified nucleotides or modified nucleotides, whereby if modified, the modification is different from the modification of the nucleotides at the even nucleotide positions of the second strand. Therefore the second strand starts at the 5' end with a non-modified nucleotide in the above sense. In a more preferred embodiment, the modification of the modified nucleotides of the first and the second strand is the same and the modification of the non-modified nucleotides of the first and the second strand is also the same. In a preferred embodiment the 5' end of the antisense strand has a OH-group which preferably may be phosphorylated in a cell, preferably in a target cell, where the nucleic acid molecule of the present invention is to be active or functional, or has a phosphate group. The 5' end of the sense strand is preferably also modified, more preferably modified as disclosed herein. Any or both of the 3' ends have, in an embodiment, a terminal phosphate.

It is within the present invention that the double-stranded structure is formed by two separate strands, i.e. the first and the second strand. However, it is also with in the present invention that the first strand and the second strand are covalently linked to each other. Such linkage may occur between any of the nucleotides forming the first strand and second strand, respectively. However, it is preferred that the linkage between both strands is made closer to one or both ends of the double-stranded structure. Such linkage can be formed by covalent or non-covalent linkages. Covalent linkage may be formed by linking both strands one or several times and at one or several positions, respectively, by a compound preferably selected from the group comprising methylene blue and bifunctional groups. Such bifunctional groups are preferably selected from the group comprising bis(2-chloroethyl)amine, N-acetyl-N'-(p-glyoxylbenzoyl)cystamine, 4-thiouracile and psoralene.

In a further embodiment of the ribonucleic acid according to any of the first sub-aspects of the present invention the first strand and the second strand are linked by a loop structure.

In a preferred embodiment of the ribonucleic acid according to the first sub-aspects of the present invention the loop structure is comprised of a non-nucleic acid polymer.

In a preferred embodiment thereof the non-nucleic acid polymer is polyethylene glycol.

In an embodiment of the ribonucleic acid according to any of the first sub-aspects of the present invention the 5'-terminus of the first strand is linked to the 3'-terminus of the second strand.

In a further embodiment of the ribonucleic acid according to any of the aspects of the present invention the 3'-end of the first strand is linked to the 5'-terminus of the second strand.

In an embodiment the loop consists of a nucleic acid. As used herein, LNA as described in Elayadi and Corey (2001) Curr Opin Investig Drugs. 2(4):558-61. Review; Orum and Wengel (2001) Curr Opin Mol Ther. 3(3):239-43; and PNA are regarded as nucleic acids and may also be used as loop forming polymers. Basically, the 5'-terminus of the first strand may be linked to the 3'-terminus of the second strand. As an alternative, the 3'-end of the first strand may be linked to the 5'-terminus of the second strand. The nucleotide sequence forming said loop structure is regarded as in general not being critical. However, the length of the nucleotide sequence or the units forming such nucleotide sequence which in turn forms such loop seems to be critical for sterical reasons. Accordingly, a minimum length of four nucleotides or nucleotide analogues seems to be appropriate to form the required loop structure. In principle, the maximum number of nucleotides forming the hinge or the link between both stretches or strands to be hybridised is not limited. However, the longer a polynucleotide is, the more likely secondary and tertiary structures are formed and thus the required orientation of the stretches affected. Preferably, a maximum number of nucleotides forming the hinge is about 12 nucleotides or nucleotide analogues. It is within the disclosure of this application that any of the designs described above may be combined with any of the other designs disclosed herein and known in the art, respectively, i.e. by linking the two strands covalently in a manner that a back folding can occur through a loop structure or similar structure.

The present inventors have surprisingly found that if the loop is placed 3' of the antisense strand, i.e. the first strand of the ribonucleic acid(s) according to the present invention, the activities of this kind of RNAi are higher compared to the placement of the loop 5' of the antisense strand. Accordingly, the particular arrangement of the loop relative to the antisense strand and sense strand, i.e. the first strand and the second strand, respectively, is crucial and is thus in contrast to the understanding as expressed in the prior art where the orientation is said to be of no relevance. However, this seems not true given the experimental results presented herein. The understanding as expressed in the prior art is based on the assumption that any RNAi is subject to a processing during which non-loop linked RNAi is generated. However, if this was the case, the clearly observed increased activity of those structures having the loop placed 3' of the antisense could not be explained. Insofar a preferred arrangement in 5'→3' direction of this kind of small interfering RNAi is second strand—loop—first strand. The respective constructs may be incorporated into suitable vector systems. Preferably the vector comprises a promoter for the expression of RNAi. Preferably the respective promoter is pol III and more preferably the promoters are the U6, H1, 7SK promoter as described in Good et al. (1997) Gene Ther, 4, 45-54.

The ribonucleic acid molecule according to such first sub-aspect may be designed is to have a free 5' hydroxyl group, also referred to herein as free 5' OH-group, at the first strand. A free 5' OH-group means that the most terminal nucleotide forming the first strand is present and is thus not modified, particularly not by an end modification. Typically, the terminal 5'-hydroxy group of the second strand, respectively, is also present in an unmodified manner. In a more preferred embodiment, also the 3'-end of the first strand and first stretch, respectively, is unmodified such as to present a free OH-group which is also referred to herein as free 3' OH-group, whereby the design of the 5' terminal nucleotide is the one of any of the afore-described embodiments. Preferably such free OH-group is also present at the 3'-end of the second strand and second stretch, respectively. In other embodiments of the ribonucleic acid molecules as described previously according to the present invention the 3'-end of the first strand and first stretch, respectively, and/or the 3'-end of the second strand and second stretch, respectively, may have an end modification at the 3' end.

As used herein the terms free 5' OH-group and 3' OH-group also indicate that the respective most terminal nucleotide at the 5'end and the 3' end of the polynucleotide, respectively, i.e. either the nucleic acid or the strands and stretches, respectively, forming the double-stranded structure present an OH-group. Such OH-group may stem from either the sugar moiety of the nucleotide, more preferably from the 5'position in case of the 5' OH-group and/or from the 3' position in case of the 3' OH-group, or from a phosphate group attached to the sugar moiety of the respective terminal nucleotide. The phosphate group may in principle be attached to any OH-group of the sugar moiety of the nucleotide. Preferably, the phosphate group is attached to the 5' OH-group of the sugar moiety in case of the free 5' OH-group and/or to the 3' OH-group of the sugar moiety in case of the free 3' OH-group still providing what is referred to herein as free 5' OH-group or 3' OH-group.

As used herein with any embodiment of the first sub-aspect, the term end modification means a chemical entity added to the most 5' or 3' nucleotide of the first and/or second strand. Examples for such end modifications include, but are not limited to, inverted (deoxy) abasics, amino, fluoro, chloro, bromo, CN, CF, methoxy, imidazole, caboxylate, thioate, $C_1$ to $C_{10}$ lower alkyl, substituted lower alkyl, alkaryl or aralkyl, $OCF_3$, OCN, O—, S—, or N-alkyl; O—, S—, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

As used herein, alkyl or any term comprising "alkyl" means any carbon atom chain comprising 1 to 12, preferably 1 to 6 and more, preferably 1 to 2 C atoms.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications. The polypeptide or protein may confer further characteristics to the inventive nucleic acid molecules. Among others the polypeptide or protein may act as a ligand to another molecule. If said other molecule is a receptor the receptor's function and activity may be activated by, the binding ligand. The receptor may show internalization activity which allows an effective transfection of the ligand bound inventive nucleic acid molecules. An example for the ligand to be coupled to the inventive nucleic acid molecule is VEGF and the corresponding receptor is the VEGF receptor.

Various possible embodiments of the RNAi of the present invention having different kinds of end modification(s) are presented in the following table 1.

TABLE 1

Various embodiments of the interfering ribonucleic acid according to the present invention

| | | 1st strand/<br>1st stretch | 2nd strand/<br>2nd stretch |
|---|---|---|---|
| 1.) | 5'-end<br>3'-end | free OH<br>free OH | free OH<br>free OH |
| 2.) | 5'-end<br>3'-end | free OH<br>end modification | free OH<br>end modification |
| 3.) | 5'-end<br>3'-end | free OH<br>free OH | free OH<br>end modification |
| 4.) | 5'-end<br>3'-end | free OH<br>end modification | free OH<br>free OH |
| 5.) | 5'-end<br>3'-end | free OH<br>free OH | end modification<br>free OH |
| 6.) | 5'-end<br>3'-end | free OH<br>end modification | end modification<br>free OH |
| 7.) | 5'-end<br>3'-end | free OH<br>free OH | end modification<br>end modification |
| 8.) | 5'-end<br>3'-end | free OH<br>end modification | end modification<br>end modification |

The various end modifications as disclosed herein are preferably located at the ribose moiety of a nucleotide of the ribonucleic acid. More particularly, the end modification may be attached to or replace any of the OH-groups of the ribose moiety, including but not limited to the 2' OH, 3' OH and 5' OH position, provided that the nucleotide thus modified is a terminal nucleotide. Inverted abasics are nucleotides, either desoxyribonucleotides or ribonucleotides which do not have a nucleobase moiety. This kind of compound is, among others, described in Sternberger et al., 2002. Antisense Nucleic Acid Drug Dev. 2002; 12:131-43.

Any of the aforementioned end modifications may be used in connection with the various embodiments of RNAi depicted in table 1. In connection therewith it is to be noted that any of the RNAi forms or embodiments disclosed herein with the sense strand being inactivated, preferably by having an end modification, more preferably at the 5' end, are particularly advantageous. This arises from the inactivation of the sense strand which corresponds to the second strand of the ribonucleic acids described herein, which might otherwise interfere with an unrelated single-stranded RNA in the cell. Thus the expression and more particularly the translation pattern of the transcriptome of a cell is more specifically influenced. This effect is also referred to as off-target effect. Referring to table 1 those embodiments depicted as embodiments 7 and 8 are particularly advantageous in the above sense as the modification results in an inactivation of the—target unspecific—part of the RNAi (which is the second strand) thus reducing any unspecific interaction of the second strand with single-stranded RNA in a cellular or similar system where the RNAi according to the present invention is going to be used to knock down specific ribonucleic acids and proteins, respectively.

In a further embodiment, the nucleic acid according to the first sub-aspect has an overhang at the 5'-end of the ribonucleic acid. More particularly, such overhang may in principle be present at either or both the first strand and second strand of the ribonucleic acid according to the present invention. The length of said overhang may be as little as one nucleotide and as long as 2 to 8 nucleotides, preferably 2, 4, 6 or 8 nucleotides. It is within the present invention that the 5' overhang may be located on the first strand and/or the second strand of the ribonucleic acid according to the present application. The nucleotide(s) forming the overhang may be (a) desoxyribonucleotide(s), (a) ribonucleotide(s) or a combination thereof.

The overhang preferably comprises at least one desoxyribonucleotide, whereby said one desoxyribonucleotide is preferably the most 5'-terminal one. It is within the present invention that the 3'-end of the respective counter-strand of the inventive ribonucleic acid does not have an overhang, more preferably not a desoxyribonucleotide overhang. Here again, any of the inventive ribonucleic acids may comprise an end modification scheme as outlined in connection with table 1 and/or an end modification as outlined herein.

The second sub-aspect of the first aspect of the present invention is related to a nucleic acid according to the present invention, whereby the first stretch and/or the second stretch comprise at the 3' end a dinucleotide, whereby such dinucleotide is preferably TT. In a preferred embodiment, the length of the first stretch and/or of the second stretch consists of 18 to 23 nucleotides and more preferably the double-stranded structure comprises 18 to 23 and more preferably 19 to 21 base pairs. The design of the nucleic acid in accordance with this sub-aspect is described in more detail in, e.g., in international patent application WO 01/75164.

The third sub-aspect of the first aspect of the present invention is related to a nucleic acid according to the present invention, whereby the first and/or the second stretch comprise an overhang of 1 to 5 nucleotides at the 3' end. The design of the nucleic acid in accordance with this sub-aspect is described in more detail in international patent application WO02/44321. More preferably such overhang is a ribonucleic acid. In a preferred embodiment each of the strands and more preferably each of the stretches as defined herein has a length from 19 to 25 nucleotides, whereby more preferably the strand consists of the stretch. In a preferred embodiment, the double-stranded structure of the nucleic acid according to the present invention comprises 17 to 25 base pairs, preferably 19 to 23 base pairs and more preferably 19 to 21 base pairs.

The fourth sub-aspect of the first aspect of the present invention is related to a nucleic acid according to the present invention, whereby the first and/or the second stretch comprise an overhang of 1 to 5 nucleotides at the 3' end. The design of the nucleic acid in accordance with this sub-aspect is described in WO 02/44321.

In a fifth sub-aspect of the first aspect of the present invention the nucleic acid according to the present invention is a double-stranded nucleic acid which is a chemically synthesized double-stranded short interfering nucleic acid (siNA) molecule which directs cleavage of a [target] mRNA, preferably via RNA interference, wherein each strand of said siNA molecule is 18 to 27 or 19 to 29 nucleotides in length and said siNa molecule comprises at least one chemically modified nucleotide non-nucleotide. The design of the nucleic acid in accordance with this sub-aspect is described in more detail in international patent application WO03/070910 and UK patent 2 397 062.

In one embodiment thereof the siNA molecule comprises no ribonucleotides. In another embodiment, the siNA molecule comprises one or more nucleotides. In another embodiment chemically modified nucleotide comprises a 2'-deoxy nucleotide. In another embodiment chemically modified nucleotide comprises a 2'-deoxy-2'-fluoro nucleotide. In another embodiment chemically modified nucleotide comprises a 2'-O-methyl nucleotide. In another embodiment chemically modified nucleotide comprises a phosphorothioate internucleotide linkage. In a further embodiment the non-nucleotide comprises an abasic moiety, whereby preferably the abasic moiety comprises an inverted deoxyabasic moiety. In another embodiment non-nucleotide comprises a glyceryl moiety.

In a further embodiment, the first strand and the second strand are connected via a linker molecule. Preferably, the linker molecule is polynucleotide linker. Alternatively, the linker molecule is a non-nucleotide linker.

In a further embodiment of the nucleic acid according to the fifth sub-aspect, the pyrimidine nucleotides in the second strand are 2'-O-methyl pyrimidine nucleotides.

In a further embodiment of the nucleic acid according to the fifth sub-aspect, the purine nucleotides in the second strand are 2'-deoxy purine nucleotides.

In a further embodiment of the nucleic acid according to the fifth sub-aspect, the pyrimidine nucleotides in the second strand are 2'-deoxy-2'-fluoro pyrimidine nucleotides.

In a further embodiment of the nucleic acid according to the fifth sub-aspect, the second strand includes a terminal cap moiety at the 5' end, the 3' end or both the 5' end and the 3' end.

In a further embodiment of the nucleic acid according to the fifth sub-aspect, the pyrimidine nucleotides in the first strand are 2'-deoxy-2'-fluoro pyrimidine nucleotides.

In a further embodiment of the nucleic acid according to the fifth sub-aspect, the purine nucleotides in the first strand are 2'-O-methyl purine nucleotides.

In a further embodiment of the nucleic acid according to the fifth sub-aspect, the purine nucleotides in the first strand are 2'-deoxy purine nucleotides.

In a further embodiment of the nucleic acid according to the fifth sub-aspect, the first strand comprises a phosphorothioate internucleotide linkage at the 3' end of the first strand.

In a further embodiment of the nucleic acid according to the fifth sub-aspect, the first strand comprises a glyceryl modification at the 3' end of the first strand.

In a further embodiment of the nucleic, acid according to the fifth sub-aspect, about 19 nucleotides of both the first and the second strand are base-paired and wherein preferably at least two 3' terminal nucleotides of each strand of the siNA molecule are not base-paired to the nucleotides of the other strand. Preferably, each of the two 3' terminal nucleotides of each strand of the siNA molecule are 2'-deoxy-pyrimidines. More preferably, the 2'deoxy-pyrimidine is 2' deoxy-thymidine.

In a further aspect of the nucleic acid according to the fifth sub-aspect, the 5' end of the first strand comprises a phosphate group.

In one embodiment particularly of the fifth sub-aspect of the nucleic acid according to the present invention, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single-stranded, the percent modification can be based upon the total number of nucleotides present in the single-stranded siNA molecules. Likewise, if the siNA molecule is double-stranded, the percent modification can be based upon the total number of nucleotides present in the sense strand, antisense strand, or both the sense and antisense strands.

In a non-limiting example, the introduction of chemically-modified nucleotides into nucleic acid molecules particularly of the fifth sub-aspect of the nucleic acid according to the present invention provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

Preferably in connection with the fifth sub-aspect of the nucleic acid according to the present invention, the antisense strand, i.e. the first strand, of a siNA molecule of the invention can comprise a phosphorothioate internucleotide linkage at the 3'-end of said antisense region. The antisense strand can comprise about one to about five phosphorothioate internucleotide linkages at the 5'-end of said antisense region. The 3'-terminal nucleotide overhangs of a siNA molecule of the invention can comprise ribonucleotides or deoxyribonucleotides that are chemically-modified at a nucleic acid sugar, base or backbone. The 3'-terminal nucleotide overhangs can comprise one or more universal base ribonucleotides. The 3'-terminal nucleotide overhangs can comprise one or more acyclic nucleotides.

It will be acknowledged by the ones skilled in the art that particularly the embodiment of the present invention which comprises a loop made of nucleotides is suitable to be used and expressed by a vector. Preferably, the vector is an expression vector. Such expression vector is particular useful in any gene therapy approach. Accordingly, such vector can be used for the manufacture of a medicament which is preferable to be used for the treatment of the diseases disclosed herein. It will, however, also be acknowledged by the ones skilled in the art that any embodiment of the nucleic acid according to the present invention which comprises any non-naturally occurring modification cannot immediately be used for expression in a vector and an expression system for such vector such as a cell, tissue, organ and organism. However, it is within the present invention that the modification may be added to or introduced into the vector derived or vector expressed nucleic acid according to the present invention, after the expression of the nucleic assay by the vector. A particularly preferred vector is a plasmid vector or a viral vector. The technical teaching on how to use siRNA molecules and RNAi molecules in an expression vector is, e.g., described in international patent application WO 01/70949. It will be acknowledged by the ones skilled in the art that such vector is preferably useful in any method either therapeutic or diagnostic where a sustained presence of the nucleic acid according to the present invention is desired and useful, respectively, whereas the non-vector nucleic acid according to the present invention and in particular the chemically modified or chemically synthesized nucleic acid according to the present invention is particularly useful where the transient presence of the molecule is desired or useful.

Methods for the synthesis of the nucleic acid molecule described herein are known to the ones skilled in the art. Such methods are, among others, described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, *Methods Mol. Bio.,* 74, 59, Brennan et al., 1998, *Biotechnol Bioeng.,* 61, 33-45, and Brennan, U.S. Pat. No. 6,001, 311. All of these references are incorporated herein by reference.

In a further aspect the present invention is related to lipoplexes comprising the nucleic acid according to the present invention. Such lipoplexes consist of one or several nucleic acid molecules and one or several liposomes. In a preferred embodiment a lipoplex consists of one liposome and several nucleic acid molecules.

The lipoplex can be characterised as follows. The lipoplex according to the present invention has a zeta-potential of about 40 to 55 mV, preferably about 45 to 50 mV. The size of the lipoplex according to the present invention is about 80 to 200 nm, preferably of about 100 to 140 nm, and more preferably of about 110 nm to 130 nm, as determined by dynamic light scattering (QELS) such as, e.g., by using an N5 submicron particle size analyzer from Beckman Coulter according to the manufacturer's recommendation.

The liposome as forming part of the lipoplex according to the present invention is preferably a positively charged liposome consisting of a) about 50 mol % β-arginyl-2,3-diaminopropionic acid-N-palmityl-N-oleyl-amide trihydrochloride, preferably β-(L-arginyl)-2,3-L-diaminopropionic acid-N-palmityl-N-oleyl-amide tri-hydrochloride, b) about 48 to 49 mol % 1,2-diphytanoyl-sn-glycero-3-phosphoethanolamine (DPhyPE), and c) about 1 to 2 mol % 1,2-distearoyl-sn-glycero-3-phosphoethanolamine-polyethylen-glycole, preferably N-(Carbonyl-methoxypolyethyleneglycol-2000)-1,2-distearoyl-sn-glycero-3-phosphoethanolamine sodium salt.

The lipoplex and lipid composition forming the liposomes is preferably contained in a carrier. However, the lipoplex can also be present in a lyophilised form. The lipid composition contained in a carrier usually forms a dispersion. More preferably, the carrier is an aqueous medium or aqueous solution as also further characterised herein. The lipid composition typically forms a liposome in the carrier, whereby such liposome preferably also contains the carrier inside.

The lipid composition contained in the carrier and the carrier, respectively, preferably has an osmolarity of about 50 to 600 mosmole/kg, preferably about 250-350 mosmole/kg, and more preferably about 280 to 320 mosmole/kg.

The liposomes preferably formed by the first lipid component and optionally also by the first helper lipid, preferably in combination with the first lipid component, preferably exhibit a particle size of about 20 to 200 nm, preferably about 30 to 100 nm, and more preferably about 40 to 80 nm.

Furthermore, it will be acknowledged that the size of the particles follows a certain statistical distribution.

A further optional feature of the lipid composition in accordance with the present invention is that the pH of the carrier is preferably from about 4.0 to 6.0. However, also other pH ranges such as from 4.5 to 8.0, preferably from about 5.5 to 7.5 and more preferably about 6.0 to 7.0 are within the present invention.

For realizing these particular features various measures may be taken. For adjusting the osmolarity, for example, a sugar or a combination of sugars is particularly useful. Insofar, the lipid composition of the present invention may comprise one or several of the following sugars: sucrose, trehalose, glucose, galactose, mannose, maltose, lactulose, inulin and raffinose, whereby sucrose, trehalose, inulin and raffinose are particularly preferred. In a particularly preferred embodiment the osmolarity mostly adjusted by the addition of sugar is about 300 mosmole/kg which corresponds to a sucrose solution of 270 mM or a glucose solution of 280 mM. Preferably the carrier is isotonic to the body fluid into which such lipid composition is to be administered. As used herein the term that the osmolarity is mostly adjusted by the addition of sugar means that at least about 80%, preferably at least about 90% of the osmolarity is provided by said sugar or a combination of said sugars.

If the pH of the lipid composition of the present invention is adjusted, this is done by using buffer substances which, as such, are basically known to the one skilled in the art. Preferably, basic substances are used which are suitable to compensate for the basic characteristics of the cationic lipids and more specifically of the ammonium group of the cationic head group. When adding basic substances such as basic amino acids and weak bases, respectively, the above osmolarity is to be taken into consideration. The particle size of such lipid composition and the liposomes formed by such lipid composition is preferably determined by dynamic light scattering such as by using an N5 submicron particle size analyzer from Beckman Coulter according to the manufacturer's recommendation.

If the lipid composition contains one or several nucleic acid(s), such lipid composition usually forms a lipoplex complex, i.e. a complex consisting of a liposome and a nucleic acid. The more preferred concentration of the overall lipid content in the lipoplex in preferably isotonic 270 mM sucrose or 280 mM glucose is from about 0.01 to 100 mg/ml, preferably 0.01 to 40 mg/ml and more preferably 0.01 to 25 mg/ml. It is to be acknowledged that this concentration can be increased so as to prepare a reasonable stock, typically by a factor of 2 to 3. It is also within the present invention that based on this, a dilution is prepared, whereby such dilution is typically made such that the osmolarity is within the range specified above. More preferably, the dilution is prepared in a carrier which is identical or in terms of function and more specifically osmolarity similar to the carrier used in connection with the lipid composition or in which the lipid composition is contained. In the embodiment of the lipid composition of the present invention whereby the lipid composition also comprises a nucleic acid, preferably a functional nucleic acid such as, but not limited to, a siRNA, the concentration of the functional nucleic acid, preferably of siRNA in the lipid composition is about 0.2 to 0.4 mg/ml, preferably 0.28 mg/ml, and the total lipid concentration is about 1.5 to 2.7 mg/ml, preferably 2.17 mg/ml. It is to be acknowledged that this mass ratio between the nucleic acid fraction and the lipid fraction is particularly preferred, also with regard to the charge ratio thus realized. In connection with any further concentration or dilution of the lipid composition of the present invention, it is preferred that the mass ratio and the charge ratio, respectively, realized in this particular embodiment is preferably maintained despite such concentration or dilution.

Such concentration as used in, for example, a pharmaceutical composition, can be either obtained by dispersing the lipid in a suitable amount of medium, preferably a physiologically acceptable buffer or any carrier described herein, or can be concentrated by appropriate means. Such appropriate means are, for example, ultra filtration methods including cross-flow ultra-filtration. The filter membrane may exhibit a pore width of 1.000 to 300.000 Da molecular weight cut-off (MWCO) or 5 nm to 1 µm. Particularly preferred is a pore width of about 10.000 to 100.000 Da MWCO. It will also be acknowledged by the one skilled in the art that the lipid composition more specifically the lipoplexes in accordance with the present invention may be present in a lyophilized form. Such lyophilized form is typically suitable to increase the shelve life of a lipoplex. The sugar added, among others, to provide for the appropriate osmolarity, is used in connection therewith as a cryo-protectant. In connection therewith it is to be acknowledged that the aforementioned characteristics of osmolarity, pH as well as lipoplex concentration refers to the dissolved, suspended or dispersed form of the lipid composition in a carrier, whereby such carrier is in principle any carrier described herein and typically an aqueous carrier such as water or a physiologically acceptable buffer, preferably an isotonic buffer or isotonic solution.

Apart from these particular formulations, the nucleic acid molecules according to the present invention may also be formulated in pharmaceutical compositions as known in the art.

Accordingly, the nucleic acid molecules according to the present invention can preferably be adapted for use as medicaments and diagnostics, alone or in combination with other therapies. For example, a nucleic acid molecule according to the present invention can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Memb. Biol., 16, 129-140; Hofland and Huang, 1999, Handb. Exp. Pharmacol., 137, 165-192; and Lee et al., 2000, ACS Symp. Ser., 752, 184-192 all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not limited to, encapsulation in liposomes, by iontophoresis, or by incorporation into other vehicles, such as hydrogels, cyclodextrins (see for example Gonzalez et al., 1999, Bioconjugate Chem., 10, 1068-1074), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262. The molecules of the instant invention can be used as pharmaceutical agents. Preferably, pharmaceutical agents prevent, modulate the occurrence, or treat (alleviate a symptom to some extent, preferably all of the symptoms) of a disease state in a subject.

Thus, there is provided a pharmaceutical composition comprising one or more nucleic acid(s) according to the present invention in an acceptable carrier, such as a stabilizer, buffer, and the like. The polynucleotide(s) or nucleic acid(s) of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

There are further provided pharmaceutically acceptable formulations of the nucleic acid molecules according to the present invention. These formulations include salts of the above compounds, e.g., acid addition salts, for example, salts of hydrochloric, hydrobromic, acetic acid, and benzene sulfonic acid.

A pharmacological or pharmaceutically acceptable composition or formulation preferably refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siNA molecules siRNA molecules of the invention to an accessible diseased tissue. The rate of entry of a drug, such as the nucleic acid molecules of the present invention, into the circulation has been shown to be a function of molecular weight or size. The use of a liposome or other drug carrier comprising the nucleic acid(s) according to the present invention can potentially localize the drug, for example, in certain tissue types, such as neoplastic tissue(s). A liposome formulation that can facilitate the association of drug with the surface of cells, such as lymphocytes and macrophages is also useful. This approach can provide enhanced delivery of the drug to target cells by taking advantage of the specificity of macrophage and lymphocyte immune recognition of abnormal cells, such as cells forming the neoplastic tissue.

By "pharmaceutically acceptable formulation" is preferably meant a composition or formulation that allows for the effective distribution of the nucleic acid molecules according to the present invention in the physical location most suitable for their desired activity. Non-limiting examples for agents suitable for formulation with the nucleic acid molecules according to the present invention include: P-glycoprotein inhibitors (such as Pluronic P85), which can enhance entry of drugs into the CNS (Jollict-Riant and Tillement, 1999, Fundam. Clin. Pharmacol., 13, 16-26); biodegradable polymers, such as poly (DL-lactide-co-glycolide) microspheres for sustained release delivery after intracerebral implantation (Emerich, D F et al., 1999, Cell Transplant, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies for the nucleic acid molecules of the present invention include material described in Boado et al., 1998, J. Pharm. Sci., 87, 1308-1315; Tyler et al., 1999, FEBS Lett., 421, 280-284; pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058.

There is also provided the use of a composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24780; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

There are moreover provided herein compositions prepared for storage of administration that include a pharmaceutically effective amount of the desired compounds such as the nucleic acid molecules according to the present invention, in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or threat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg. body weight/day of active ingredients is administered dependent upon potency of the negatively charged polymer.

The nucleic acid molecules according to the present invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrahecal injection or infusion techniques and the like. In addition, there is provided a pharmaceutical formulation comprising a nucleic acid molecule of the invention and a pharmaceutically acceptable carrier. One or more nucleic acid molecules according to the present invention can be present in association with one or more non-toxic pharmaceutically acceptable carriers and/or diluents and/or adjuvants, and if desired other active ingredients. The pharmaceutical compositions containing nucleic acid molecules according to the present invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the person skilled in the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials such as the nucleic acid(s) according to the present invention in a mixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxyoctanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and coloring agents, can also be present.

Pharmaceutical compositions of the invention can also be in the form of oil-in-water emulsions. The oily phase can be a vegetable oil or a mineral oil or mixture of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels for the medicament and pharmaceutical composition, respectively, can be determined by those skilled in the art by routine experimentation.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy. For administration of the medicament according to the present invention to non-human animals such as dogs, cats, horses, cattle, pig, goat, sheep, mouse, rat, hamster and guinea pig, the composition can preferably also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In one embodiment, there are provided compositions suitable for administering the nucleic acid molecules according to the present invention to specific cell types, whereby such compositions typically incorporate one or several of the following principles and molecules, respectively. For example, the asialoglycoprotein receptor (ASGPr) (Wu and Wu, 1987, *J. Biol. Chem.* 262, 4429-4432) is unique to hepatocytes and binds branched galactose-terminal glycoproteins, such as asialoorosomucoid (ASOR). In another example, the folate receptor is overexpressed in many cancer cells. Binding of such glycoproteins, synthetic glycoconjugates, or folates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell*, 22, 611-620; Connolly et al., 1982, *J. Biol. Chem.*, 257, 939-945). Lee and Lee, 1987. *Glycoconjugate J.* 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, *J. Med. Chem.*, 24, 1388-1395). The use of galactose, galactosamine, or folate based conjugates to transport exogenous compounds across cell membranes can provide a targeted delivery approach to, for example, the treatment of liver disease, cancers of the liver, or other cancers. The use of bioconjugates can also provide a reduction in the required dose of therapeutic compounds required for treatment. Furthermore, therapeutic bioavailability, pharmacodynamics, and pharmacokinetic parameters can be modulated through the use of nucleic acid bioconjugates of the invention. Non-limiting examples of such bioconjugates are described in Vargeese et al., U.S. Ser. No. 10/201,394, filed Aug. 13, 2001; and Matulic-Adamic et al., U.S. Ser. No. 60/362,016, filed Mar. 6, 2002.

The nucleic acid molecules, in their various embodiments, according to the present invention, the vector, cell, medicament, composition and in particular pharmaceutical composition containing the same, tissue and animal, respectively, according to the present invention containing such (a) nucleic acid molecule(s) can be used in both for therapeutic use as well as in the diagnostic and research field.

In so far the present invention is, in a further aspect, related to the treatment of diseases, whereby such treatment involves the use of the nucleic acid molecules, in their various embodiments, the vector, the cell, the medicament, the composition and in particular pharmaceutical composition, each in accordance with the present invention.

Such diseases comprise, but are not limited to, proliferative disorders, hyperplasia of epithelial and hematopoietic cells, including cancer, atherosclerosis, inflammatory diseases such as allergy or during immunodeficiency conditions, and viral infections. In case of viral infections, such infections are preferably those which are mediated by or associated with double-stranded DNA viruses the replication of which depends on Orc and more specifically Orc-1.

As preferably used herein, proliferative disorders are defined as any cellular disorder in which the cells within an tissues/organ proliferate more rapidly than the surrounding normal tissue growth. The proliferative disorders, include but are not limited to neoplasms. A neoplasm is an abnormal tissue growth, generally forming a distinct mass that grows by cellular proliferation more rapidly than normal tissue growth, i.e. than the growth shown by normal and more specifically non-diseased tissue. Neoplasms show partial or total lack of structural organization and functional coordination with normal, more specifically non-diseased or non-neoplastic tissue.

Neoplasms also include all common forms of cancer such as bladder cancer, melanoma, breast cancer, non-Hodgkin lymphoma, colon and rectal cancer, pancreatic cancer, endometrial cancer, prostate cancer, kidney (renal cell) cancer, skin cancer (non-melanoma), leukemia, thyroid cancer, lung cancer. Further proliferative disorders include, but are not limited to neurofibromatosis, all diseases related to vascular proliferation including non-physiological endothelial proliferation (angiogenesis), and atherosclerosis.

More preferably neoplastic diseases or neoplasms are as follows:

Adenoma, angiofibroma, arachnoid cysts, astrocytoma, bone neoplasms, Bowen's disease, breast cyst, breast neoplasms, breast neoplasms, male, Burkitt lymphoma, carcinoid tumor, carcinoma, carcinoma, Merkel cell, carcinoma, non-small-cell lung carcinoma, small cell lung cell carcinoma, cementoma, choledochal cyst, chondroma, chondrosarcoma, chordoma, craniopharyngioma, cysts, dermoid cyst, digestive system neoplasms, ear neoplasms, endocrine gland neoplasms, endometrial neoplasms, ependymoma, epidermal cyst, fibromatosis, aggressive, fibromatosis, juvenile hyaline (not on MeSH), gastrointestinal neoplasms, gastrointestinal stromal tumors, genital neoplasms, female, genital neoplasms, male, glioblastoma, glioma, hamartoma, hamartoma syndrome, multiple, head and neck neoplasms, hemangioma, histiocytoma, benign fibrous, histiocytoma, malignant fibrous, Hodgkin disease, Hutchinson's melanotic freckle, insulinoma, Krukenberg tumor, laryngeal neoplasms, leiomyoma, leiomyosarcoma, leukemia, lipoma, lung neoplasms, lymphangioma, lymphoma, lymphoma, non-Hodgkin, mediastinal cyst, medulloblastoma, melanoma, melanoma, amelanotic, meningioma, mesothelioma, mouth neoplasms, multiple myeloma, myoma, myxoma, neoplasm metastasis, neoplasm, residual, neoplasms, neoplasms, connective and soft tissue, nervous system neoplasms, neurilemmoma, neuroblastoma, neuroendocrine tumors, neuroma, acoustic, nevus, odontogenic tumors, osteosarcoma, otorhinolaryngologic neoplasms, ovarian cysts, ovarian neoplasms, Paget's disease, mammary, papilloma, paraganglioma, paraneoplastic syndromes, nervous system, pheochromocytoma, pilonidal sinus, popliteal cyst, precancerous conditions, pseudomyxoma peritonei, ranula, rectal neoplasms, respiratory tract neoplasms, retinoblastoma, rhabdoid tumor, rhabdomyosarcoma, sarcoma, sarcoma, Ewing's, Sezary syndrome, skin neoplasms, Tarlov cysts, teratoma, thymoma, tonsillar neoplasms, tuberous sclerosis, urologic neoplasms, uterine cervical dysplasia, uterine cervical neoplasms, Wilms tumor, vulvar neoplasms.

In addition, hyperplasia include benign prostatic hyperplasia, breast hyperplasia including atypical usual ductal hyperplasia, compensatory liver hyperplasia, congenital adrenal hyperplasia, endometrial hyperplasia including polycystic ovary syndrome and endometrial adenocarcinoma, focal epithelial hyperplasia, Heck's disease, and sebaceous hyperplasia.

The diseases associated with or caused by DNA viruses include, but are not limited to virus infections such as Bell palsy, Burkitt lymphoma, chickenpox, cytomegalovirus infections, ecthyma, contagious, encephalitis, herpes simplex, Epstein-Barr virus infections, erythema infectiosum, exanthema subitum, herpes labialis, herpes simplex, herpes zoster, herpes zoster oticus, Herpesviridae infections, infectious mononucleosis, molluscum contagiosum, polyomavirus infections, smallpox, warts, human papillomavirus HPV, infectious mononucleosis, EBV-associated malignancies including but not limited to nasopharyngeal carcinoma and chronic fatigue syndrome; and, for KSHV which is also known as HHV8, Kaposi's sarcoma.

It is within the present invention that the nucleic acid molecules according to the instant application are used either as the sole pharmaceutically active agent or together with one or several other pharmaceutically active agents It is to be acknowledged that the various diseases described herein for the treatment and prevention of which the pharmaceutical composition according to the present invention may be used, are also those diseases for the prevention and/or treatment of which the medicament described herein can be used, and vice versa.

As used herein the term treatment of a disease shall also comprise prevention of such disease.

Further features, embodiments and advantages may be taken from the following figures and examples, whereby FIG. 1 shows the result of a Western blot analysis of a knockdown experiment using different Orc-1 specific siRNA molecules;

FIG. 2A shows a diagram indicating the number of HeLa cells upon treatment of HeLa cell cultures with Orc-1 specific siRNA-lipoplexes (ORC1-3 and ORC1-4) and two negative controls (example 5);

FIG. 2B shows a panel of microphotographs of the HeLa cells treated as described in example 5 on day 5.

FIG. 4A shows a panel of microphotographs of HUVEC cells treated with different siRNA containing lipoplexes and visualized by nuclear counterstaining with Sytox green reagent;

FIG. 4B shows the result of a Western blot analysis to demonstrate Orc-1 knockdown in the cells depicted in FIG. 4A with PTEN being the loading control;

FIG. 5 shows the result of a Western blot analysis comparing the effects of 19 mer specific and 23 mer specific Orc-1 siRNA molecules;

FIG. 6A shows the experimental design of an in vivo study using an ectopic (subcutaneous) prostate mouse model;

FIG. 6B shows a diagram indicating tumor volume over time for groups of mice treated either with Orc-1 specific siRNA containing lipoplexes or with sucrose;

FIG. 6C shows a diagram indicating body weight over time for groups of mice treated with either Orc-1 specific siRNA containing lipoplexes or sucrose;

EXAMPLE 1

Materials and Methods

Antibodies

The following antibodies were used in this study:

anti-Orc-1: rabbit polyclonal serum, raised against human Orc1 (recombinant baculovirus infection of Sf9 cells)

rabbit anti-PTEN (Ab-2, Neomarkers).

anti-cleaved PARP which is used for indicating apoptotic signaling (Cell Signaling Technologies).

anti-Hsp60 (BD Laboratories)

Cell Lines

HUVEC cells were obtained from Lonza and cultivated according to the manufacturer's recommendations. HeLa cells (CCL2, ATCC) were maintained in EMEM medium+10% FBS under standard conditions.

DU-145 cells were obtained from ATCC (HTB-81).

The BxPC-3 tumor cell line was provided by Oncodesign and was originally obtained from the American Tissue and Cell Collection (ATCC, Rockville, Md., USA). The BxPC-3 cell line is a pancreas adenocarcinoma isolated from a 61-year old Caucasian female patient.

Proliferation Assay

HeLa cells were seeded on 10 cm petri dishes at a density of 380,000 cells/plate the day before transfection. Transfection was carried as described below; on day 2 post transfection, cells were trypsinized and, counted (Casy Cell counter) and for all samples tested cell number was equally adjusted to 200,000 cells/plate for re-plating. Cells were maintained in culture for additional 72-192 h and cells were counted on the respective day post transfection. An aliquot of the counted cell samples was used for protein extracts and subsequent Western blotting in order to monitor target-specific protein knockdown.

Transfection of Cultured Cells

Transfections and proteins extracts for immunoblotting were carried out as previously described (Santel et al, Gene Ther 13(18): 1360-1370 (2006)).

Delivery of siRNA Containing Lipoplexes in Tumor Bearing Mice

Figure 7:
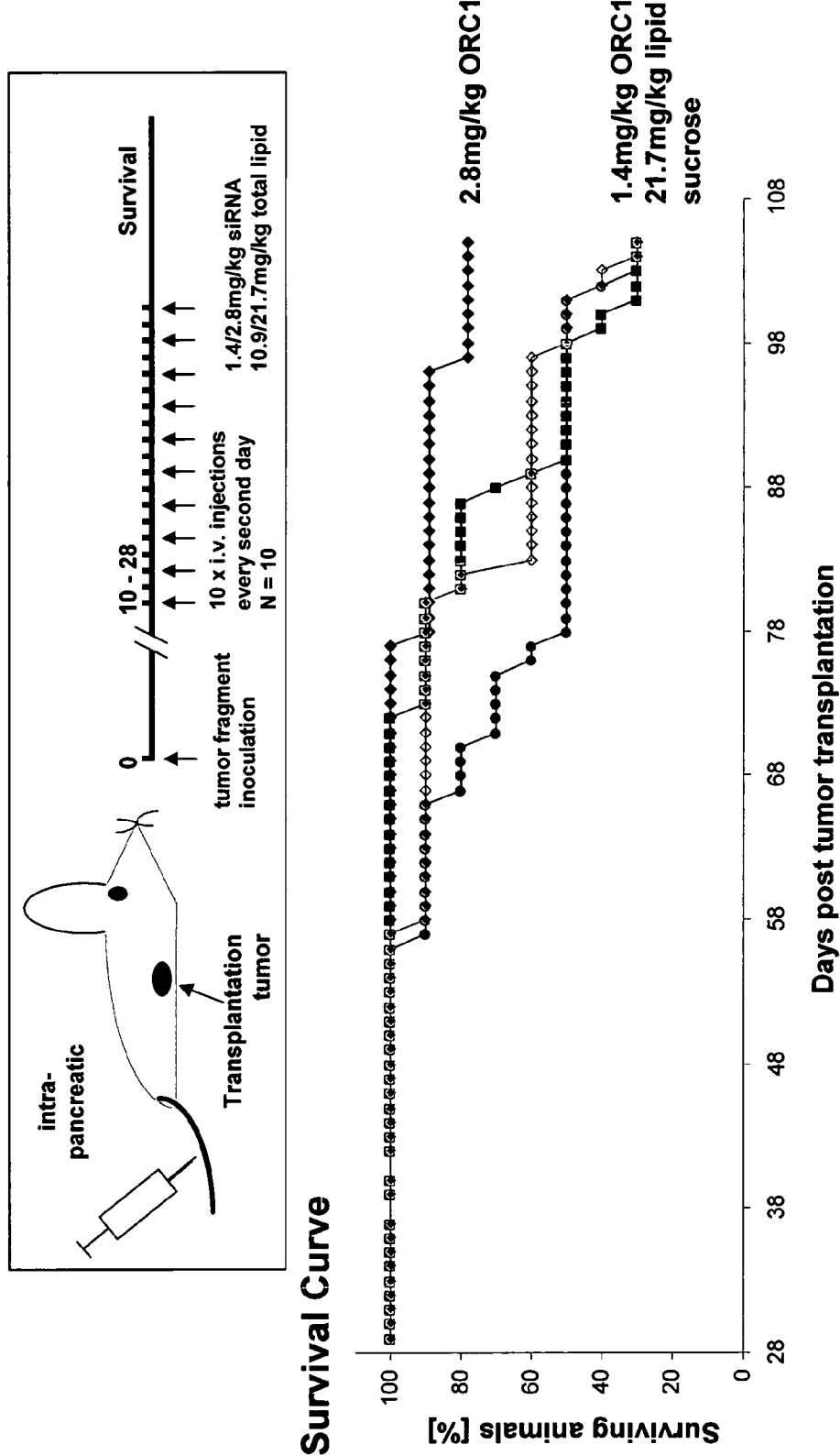
FIG. 7A shows the experimental design of an in vivo study using an orthotopic pancreas carcinoma mouse model.
FIG. 7B shows a diagram illustrating the surviving animal in % over days post tumor transplantation for various formulations containing Orc-1 specific siRNA containing lipoplexes.

In vivo delivery experiments using siRNA containing lipoplexes were performed by administering siRNA lipoplexes intravenously through single tail vein injection of 200 µl solution at a final dose of 1.88 mg/kg siRNA-Cy3 and 14.5 mg/kg lipid. In connection with the results depicted in FIGS. 6 and 7 delivery conditions were as follows: FIG. 6 (DU-145 s.c.): 2.8 mg/kg siRNA complexed with 21.7 mg/kg were injected by i.v. bolus on ten consecutive days. FIG. 7 (BxPC-3 ipancr): 2.8 mg/kg siRNA complexed with 21.7 mg/kg lipid or 1.4 mg/kg siRNA formulated with 10.9 mg/kg lipid; both applied by i.v. bolus every other day over a period of 20 days. Mice were sacrificed 4 hours post injection and fluorescence uptake examined by microscopy on formalin fixed, paraffin embedded tissue sections.

Immunofluorescence Analysis and Microscopy

For immunofluorescence analysis on culture cells after transfection, cells were rinsed twice with Dulbecco's PBS (phosphate buffered saline), fixed with 4% formaldehyde/PBS 15 minutes at room temperature, rinsed three times and permeabilized for 15 minutes in PBTD (PBS with 0.1% Triton X-100, 0.05% sodium deoxycholate), then blocked for 30 minutes with PBTB (PBS with 0.1% Trition X-100, 3% bovine serum albumin). Slides were incubated with primary antibody 2 hours at 37° C., rinsed four times with PBTB, incubated 2 hours at 37° C. in FITC-/Cy3-conjugated anti-rabbit or anti-mouse IgG (Jackson Immunochemicals; 1:200 in PBTB), washed extensively in PBS, counterstained with Sytox Green dye (Molecular Probes, 100 nM) for chromosome visualization and examined by epifluorescence on a Zeiss Axioplan or confocal (Zeiss LSM510 Meta) microscope. Phase contrast light microscopy was carried out with a Zeiss Axioplan microscope.

Determination of Tumor Size, Survival and Body Weight

Tumor size, survival and body weight was determined as described in Santel et al. (Gene Ther 13(18): 1360-1370 (2006)).

During the course of the BxPC-3 experiment, animals were killed by cervical dislocation under anaesthesia with isoflurane if any of the following occurred:

signs of suffering such as cachexia, weakening, difficulty moving or eating, compound toxicity such as hunching, convulsions, 15% body weight loss for 3 consecutive days or 20% body weight loss for 1 day.

An autopsy namely macroscopic examination of heart, lungs, liver, spleen, kidneys and gastro-intestinal tract was performed on all sacrificed (scheduled) mice in the study, and, if feasible, on all moribund/found dead mice. Autopsy observations were recorded.

Survival Parameters

Survival curves of mice were drawn. The parameters expressed as a percent (T/C %) and as the increased life span values (% ILS) of the control evaluation provide measures of effectiveness of the test substances. Survival systems indicate a degree of success when T/C percents exceed 125 and ILS percents exceed 25. C is the median survival times of control (i.e. vehicle treated) animals. T is the median survival times of animals treated with test substance. T/C % and ILS % were calculated with the following formulas:

$$ILS\% = (T-C)/C \times 100$$

$$T/C\% = T/C \times 100$$

Tumor Xenograft Experiments

DU-145 Model:

Male Hsd:NMRI-nu/nu mice (8 weeks old) were used in this study. For tumor therapy experiments on established tumor xenografts, a total of $2.0 \times 10^6$ tumor cells/100 µl PBS were transplanted subcutaneously. Tumor volume was determined using a caliper and calculated according to the formula volume=(length×width$^2$)/2. For tumor therapy experiments siRNA-lipoplex solution was administered i.v. by low pressure, low volume tail vein injection. Established DU-145 tumor mice received a daily 300 µl injection for a 30 g mouse (single dose 2.8 mg/kg siRNA and 21.7 mg/kg lipid). All animal experiments in this study were performed according to approved protocols and in compliance with the guidelines of the Landesamt für Arbeits-, Gesundheitsschutz and technische Sicherheit Berlin, Germany (No. G0077/05).

BxPC-3 Model (Oncodesign):

Induction of BxPC-3 tumors in female SCID mice Ten millions of BxPC-3 tumor cells re-suspended in McCoy's 5A medium in a volume of 0.2 ml were subcutaneously inoculated in the right flank of 5 female SCID mice 24 h after a whole body irradiation with a γ-radiation emitting source (1.8 Gy, $^{60}$Co, INRA BRETENNIERES, Dijon, France). When tumor sizes reached a mean volume of 700-1000 mm³, tumors were surgically excised and fresh smaller tumor fragments (1-5 mg) were orthotopically implanted in the pancreas of 72 female SCID mice, 24-48 hours after whole body irradiation with a γ-radiation emitting source (1.8 Gy, $^{60}$Co, INRA BRETENNIERES, Dijon, France). Under anesthesia, the animals' abdomen was opened through a median incision under aseptic conditions and the spleen with the tail of the pancreas was gently exteriorized. One small tissue pocket was prepared in the pancreatic parenchyma as an implantation bed by a microscissor. A tumor fragment was implanted in the epiploon. The pancreas was relocated into the abdominal cavity, which was subsequently closed in 2 layers with 5-0 sutures. The day of BxPC-3 tumor fragment implantation was considered as the day 0 (D0). The treatment started on day 10 (D10).

Statistical Analysis

Data are expressed as means±s.e.m. Statistical significance of differences was determined by the Mann-Whitney U test. P values<0.05 were considered statistically significant.

EXAMPLE 2

Orc-1 Specific siRNA Molecules

The siRNA molecules (AtuRNAi, see Table 1.) which are directed to the mRNA coding for Orc-1 and the various siRNA molecules directed to Luciferase and which were used in connection with the experiments and examples described herein, were synthesized by BioSpring (Frankfurt a. M., Germany) and are indicated in Table in terms of the sequences of both the first strand and the second strand forming the double-stranded nucleic acid molecules of the present invention. It will be understood that these siRNA molecules and the corresponding derivatives such as the 21 mers, 23 mer and 25 mers represent preferred embodiments of the nucleic acid molecule according to the present invention and may accordingly be used in connection with each and any aspect of the present invention.

TABLE 1

```
siRNA molecule ORC1-1:
ORC1-1B    aggaauuccaagacaucua    (SEQ.ID.No: 2)
ORC1-1A    uagaugucuuggaauuccu    (SEQ.ID.No: 3)

siRNA molecule ORC1-2:
ORC1-2B    gucccugggacagggaaga    (SEQ.ID.No: 4)
ORC1-2A    ucuuccugucccagggac     (SEQ.ID.No: 5)

siRNA molecule ORC1-3:
ORC1-3B    gauguuccuccuuucaau     (SEQ.ID.No: 6)
ORC1-3A    auugaaagggaggaacauc    (SEQ.ID.No: 7)

siRNA molecule ORC1-4:
ORC1-4B    auguuccuccuuucaaua     (SEQ.ID.No: 8)
ORC1-4A    uauugaaagggaggaacau    (SEQ.ID.No: 9)

siRNA molecule ORC1-5:
ORC1-5B    cccaccaagucuaugugca    (SEQ.ID.No: 10)
ORC1-5A    ugcacauagacuugguggg    (SEQ.ID.No: 11)
```

TABLE 1-continued

```
siRNA molecule ORC1-6:
ORC1-6B    uuuggacucacaaacaaga    (SEQ.ID.No: 68)
ORC1-6A    ucuuguuugugaguccaaa    (SEQ.ID.No: 69)

siRNA molecule ORC1-7:
ORC1-7B    ggaacagagcuuccugaga    (SEQ.ID.No: 14)
ORC1-7A    ucucaggaagcucuguucc    (SEQ.ID.No: 15)

siRNA molecule ORC1-8:
ORC1-8B    caaccuuucaacagauaua    (SEQ.ID.No: 70)
ORC1-8A    uauaucuguugaaagguug    (SEQ.ID.No: 71)

siRNA molecule LUCI:
LUCI-B     cguacgcggaauacuucga    (SEQ.ID.No: 18)
LUCI-A     ucgaaguaguccgcguacg    (SEQ.ID.No: 19)
```

A stands for the antisense strand which is also referred to herein as the first strand; B stands for the sense strand which is also referred to herein as the second strand. Please note that any sequence indicated in the instant application is presented in 5'→3' direction, if not explicitly indicated to the contrary.

Any underlined and bold printed nucleotide in the above Table 1 is modified at the 2' position such as to be 2'-O-methyl; non-underlined nucleotides are non-modified nucleotides having a OH group at the 2' position.

The siRNA molecules actually used consist of the respective B and A strand; accordingly, e.g., the Orc-1 specific siRNA ORC1-3 molecule ORC1-3 consists of the strands ORC1-3B and ORC1-3A.

The duplexes formed by the corresponding B strands and A strand lack 3'-overhangs and are chemically stabilized by alternating 2'-O-methyl sugar modifications on both strands, whereby unmodified nucleotides face modified ones on the opposite strand (Table 1) (Czaudema et al (Nucleic Acids Res 31(11): 2705-2716 (2003)).

Particularly preferred molecules according to the instant invention are ORC1-3 consisting of a duplex formed of ORC1-3B and ORC1-3A, ORC1-4 consisting of a duplex formed of ORC1-4B and ORC1-4A, ORC1-6 consisting of a duplex formed of ORC1-6B and ORC1-6A, and ORC1-7 consisting of a duplex formed of ORC1-7B and ORC1-7A,

EXAMPLE 3

Lipoplex Formulation of Orc-1 Specific siRNA Molecules

Lipoplex formulations containing Orc-1 specific siRNA molecules are also referred to as siRNA lipoplexes or siRNA$^{Orc1}$-lipoplexes herein.

The proprietary cationic lipid AtuFECT01 (β-L-arginyl-2,3-L-diaminopropionic acid-N-palmityl-N-oleyl-amide trihydrochloride, Silence Therapeutics AG), the neutral phospholipid 1,2-diphytanoyl-sn-glycero-3-phosphoethanolamine (DPhyPE) (Avanti Polar Lipids Inc., Alabaster, Ala.) and the PEGylated lipid N-(Carbonyl-methoxypolyethyleneglycol-2000)-1,2-distearoyl-sn-glycero-3-phospho-ethanolamine sodium salt (DSPE-PEG) (Lipoid GmbH, Ludwigshafen, Germany) were mixed in a molar ratio of 50/49/1 by lipid film re-hydration in 300 mM sterile RNase-free sucrose solution to a total lipid concentration of 4.34 mg/ml.

Such formulation was in case of the experiments on DU-145 (s.c.) 2.8 mg/kg siRNA complexed with 21.7 mg/kg which were injected by i.v. bolus on ten consecutive days (as depicted in FIG. 6), and in case of BxPC-3 (ipancr) 2.8 mg/kg siRNA complexed with 21.7 mg/kg lipid or 1.4 mg/kg siRNA formulated with 10.9 mg/kg lipid; both applied by i.v. bolus every other day over a period of 20 days (FIG. 7).

EXAMPLE 4

Characterization of siRNA$^{Orc1}$-lipoplexes

The Orc-1 specific siRNA molecules of example 2 which were formulated as lipoplexes in accordance with example 3, were tested for their capacity to inhibit Orc-1 expression in HUVECs. For such purpose the HUVECs were transfected with the eight different siRNA ORC1-lipoplexes of Table 1, or with the controls, at a final concentration of 20 nM for 48 hours. Cells were harvested and corresponding protein extracts subjected to SDS-PAGE and processed for Western blot. Further details may be taken from example 1. As controls lipoplexes containing a luciferase specific siRNA molecule consisting of strands LUCI-B and LUCI-A were used. PTEN served as loading control.

Figure 1:
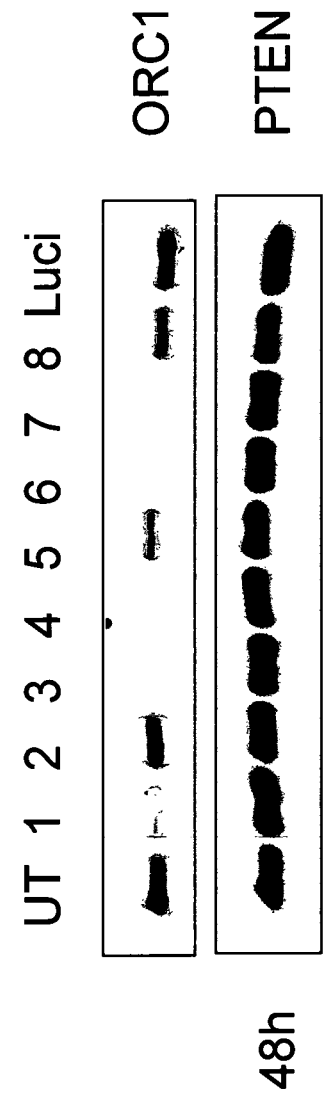

The result of the Western blot is indicated in FIG. 1.

As may be taken from FIG. 1 lipoplexes containing any of the siRNA molecules ORC1-3, ORC1-4, ORC1-6 or ORC1-7 were particularly effective in inhibiting the expression of Orc-1 in HUVEC, whereas those Orc1-specific lipoplexes containing any of ORC1-2, ORC1-5 or ORC1-8 were factually inactive. Lipoplexes containing ORC1-1 inhibited the expression of the Orc-1 mRNA to a certain extent, however, were not as effective as ORC1-3, ORC1-4, ORC1-6 or ORC1-7. From this example it may be taken that different siRNA molecules targeting different regions of the Orc-1 mRNA show different activities in terms of knockdown of the target mRNA.

EXAMPLE 5

Inhibition of HeLa Cell Proliferation by siRNA$^{Orc1}$-lipoplexes

HeLa cells were transfected with one of two highly efficacious siRNA$^{ORC1}$-lipoplexes, namely ORC1-3 and ORC1-4, and two negative controls (ORC1-5 and LUCI). The cells were transfected once at a final concentration of 15 nM for respective siRNAs. The effect of the siRNA-lipoplexes on proliferation was determined by cell counting.

The results of this experiment are depicted in FIG. 2A. Cell number (cells*10$^6$/ml) was monitored over time for indicated samples.

As may be taken from the diagram depicted in FIG. 2A treatment of HeLa with siRNA$^{ORC1-3}$- and siRNA$^{ORC1-4}$-lipoplexes resulted in a significant reduction of cell proliferation, whereas siRNA$^{ORC1-5}$ lipoplexes had factually no effect.

Microphotographs were taken on day 5 from the thus treated cells and are depicted in FIG. 2B. In accordance with the results shown in FIG. 2A, the cells treated with siRNA$^{ORC1-3}$ and siRNA$^{ORC1-4}$-lipoplexes were most affected in their growth compared to the cells treated either with the control or with siRNA$^{ORC1-5}$-lipoplexes.

EXAMPLE 6

Induction of Apoptosis by siRNA$^{Orc1}$-lipoplexes

In order to assess the effects arising from the knockdown of Orc-1 mediated by siRNA$^{Orc1}$-lipoplexes, the cells of example 5 were analyzed by Western blotting. Knockdown of Orc-1 gave rise to the generation of the cleaved PARP (Poly-ADP-Ribose-Polymerase 1), a downstream target of activated caspse-3. Therefore, this protein variant serves as a marker protein for monitoring apoptosis. Hsp60 was used as a control to demonstrate equal loading.

Figure 3:
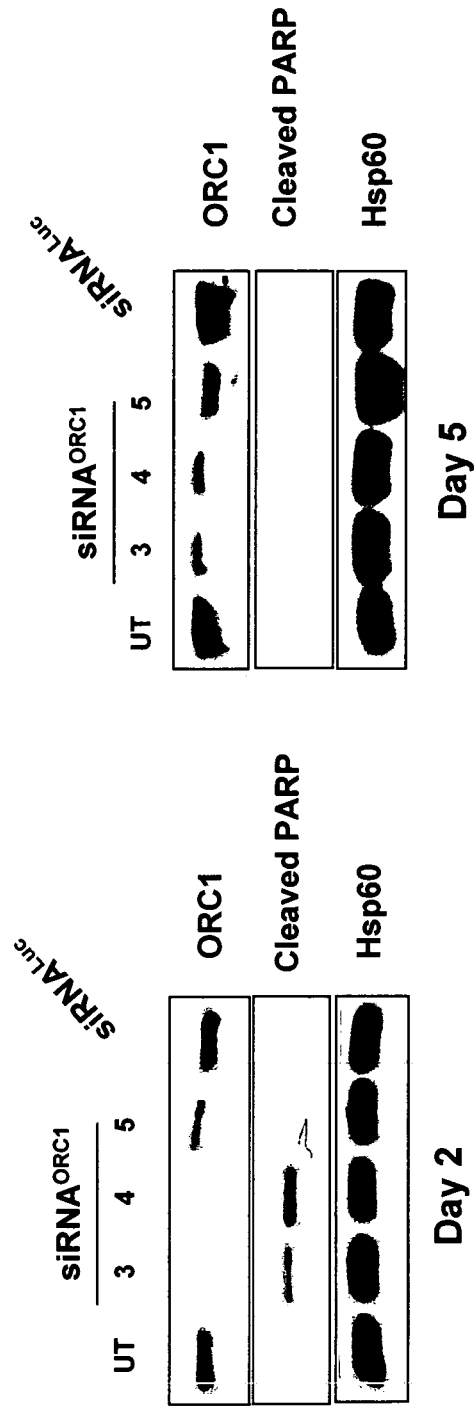
FIG. 3 shows the result of a Western blot analysis of a knockdown experiment sing different Orc-1 specific siRNA molecules on day 2 (FIG. 3A) and day 5 (FIG. 3B), and monitoring the expression of the apoptosis marker cleaved PARP in parallel.

The results are shown in FIG. 3 show, the appearance of cleaved PARP correlated with depletion of Orc-1 achieved by siRNA$^{Orc1}$-lipoplexes ORC1-3 and ORC1-4 on day 2 after single transfection in contrast to negative control samples. Reoccurred/increased level of Orc-1 on day 5 abolishes the generation of detectable levels of cleaved PARP. In other words, on day 5 the knockdown of Orc-1 was less pronounced than on day 2, but still existing. On day 5, no cleaved PARP could be detected. These results suggest that depletion of ORC-1 in proliferating cells leads to apoptosis. Therefore, induction of apoptosis might be the cause for the reduced proliferation rate for the respective two potent siRNA-lipoplexes shown in Example 5.

EXAMPLE 7

Effect of siRNA$^{Orc1}$-lipoplexes Treatment on HUVEC Proliferation

In order to further characterize the loss of function phenotype in cells lacking ORC-1 after siRNA$^{Orc1}$-lipoplexes treatment on the cellular level, HUVEC cells were transfected with the indicated siRNA$^{Orc1}$-lipoplexe ORC1-3. Lipoplex ORC1-5 as well as lipoplex LUCI served as controls. The cells were visualized by nuclear counterstaining with Sytox green reagent on day 5 post single transfection with indicated siRNA-lipoplexes at final 20 nM siRNA concentration. Microscopic evaluation of the samples revealed differences in cell number and mitotic activity reflected by the occurrence of metaphase plate figures (arrows).

The result is shown in FIG. 4A as microphotographs of the respective cultures.

As expected, treatment with siRNA$^{ORC1}$-lipoplexe ORC1-3 resulted in a decrease in the number of stained HUVEC nuclei and occurrence in "mitotic figures" (metaphase plate; arrows) in contrast to control and less potent siRNA-ORC1-5.

The cells subject to the various treatments were subsequently analysed by Western blotting. More specifically, the result is shown in FIG. 4B and proves the functionality of the lipoplexes used in this experiment.

From FIG. 4B it may be taken that the siRNA$^{Orc1}$-lipoplexe ORC1-3 is most effective in knocking down Orc-1 mRNA in HUVEC, whereas ORC1-5 is less effective.

EXAMPLE 8

Characterization of siRNA$^{Orc1}$-lipoplexe ORC1-3: Impact of the Length of the siRNA Molecule In order to test the impact of the length of the siRNA molecules contained in the siRNA$^{Orc1}$-lipoplexes on target knockdown, two variants of the ORC1-3 siRNA molecule were prepared. The first variant corresponds to the ORC1-3 siRNA molecule described in example 1 consisting of the nucleic acid molecules according to SEQ.ID.No: 6 and SEQ.ID.No.7. This first variant is also referred to herein as ORC1-3-19. The second variant consisted of the following two strands:

```
Strand B (sense strand, 5'->3'):
caaugauguuccucccuuucaau      (SEQ.ID.No: 20)

Strand A (antisense strand, 5' -> 3'):
auugaaagggaggaacaucauug      (SEQ.ID.No: 21)
```

Nucleotides which are 2'-O-methyl, are underlined and in bold.

This second variant is also referred to herein as ORC1-3-23.

HUVEC cells were transfected with corresponding siRNA lipoplexes at a concentration of either 20 nM or 5 nM. 72 h post transfection protein extracts were subjected to SDS-gel electrophoresis and ORC1 protein reduction was assessed by Western blot.

The results are shown in FIG. 5.

As may be taken from FIG. 5, the length of lipoplex ORC1-3 did not have any impact on the efficacy of the knockdown of the Orc1-mRNA at any of the two concentrations. From this it is evident that also the siRNA molecule ORC1-3-23 and the lipoplexes containing such siRNA molecules, but also any of the other ORC1 siRNA molecules described herein having a length of 23 base pairs rather than 19 base pairs may be used in accordance with the present invention. In order to generate ORC1-3-23 the initial lead sequences of Orc1-3, which could accordingly also be referred to as ORC1-3-19, and which correspond to nucleotide sequences according to, SEQ.ID.No: 6 and 7 were extended by four additional bases at the 3'-end of the RNA sequences.

EXAMPLE 9

Reduction of Tumor Growth in a Prostate Ectopic/Subcutaneous Model by Administration of siRNA$^{Orc1}$-lipoplex A subcutaneous means ectopic mouse model for prostate cancer was established by injecting cells DU-145 s.c. 21 days after tumor cell inoculation, the mice received a daily siRNA-lipoplex dose of 2.8 mg/kg siRNA and 21.7 mg/kg overall lipid. The siRNA-lipoplex dose was administered i.v. in the tail vein on days 21 to 30. The study comprised the following treatment groups with each group consisting of seven mice:
   siRNA$^{Orc1}$-lipoplex ORC1-3, vehicle control, PKN3- and CD31-siRNA-lipoplexes
The control group received 270mM sucrose applied in the same treatment schedule than siRNA-lipoplexes, i.e.300 μl i.v. bolus per 30 g mouse.

The experimental design is depicted in FIG. 6A.

The results of this experiment are shown in FIGS. 6B and 6C.

From FIG. 6B which is a diagram depicting the tumor volume from day 21 to 31 post cell challenge, i.e. after the initial tumor inoculation, it can be taken that the mice treated with siRNA$^{Orc1}$-lipoplexes ORC1-3 (19 mer) showed a significant inhibition in tumor growth compared to the sucrose, and surprisingly to the siRNA-lipoplexes targeting CD31 or PKN3 treated control group.

That such treatment was actually not toxic may be taken from FIG. 6C which is a diagram indicating the body weight of the two treatment groups on days 21 to 31 post cell challenge. From this it may be taken that there was only a minimal reduction in body weight of the siRNA$^{Orc1}$-lipoplex treated mice on day 22 and 23, whereas for the rest of the study, the body weight of the mice remained at the same level which is comparable to the one of the control group receiving sucrose.

EXAMPLE 10

Reduction of Tumor Growth in a Pancreatic Orthotopic Model by Administration of siRNA$^{Orc1}$-lipoplexe The orthotopic mouse model for pancreas carcinoma BxPC-3 which is commercially available from Oncodesign, France, was used in this experiment. In contrast to the example above, this model bears all advantages of a more clinically relevant orthotopic xenograft model, since tumor cells become implanted to the correct anatomical site of original genesis. This is a widely used model for pancreatic cancer pathogenesis (Tan, M H et al., Cancer Invest. 1986; 4(1):15-23. Ten days after tumor cell inoculation, the mice received a daily siRNA-lipoplex dose of either 1.4 mg/kg siRNA and 10.9 mg/kg overall lipid, or of 2.8 mg/kg siRNA and 21.7 mg/kg overall lipid. The siRNA-lipoplex dose was administered i.v. in the tail vein on days 10 to 28. The study comprised the following treatment groups with each group consisting of ten mice:
   siRNA$^{Orc1}$-lipoplex ORC1-3 using one of the above two dosages, and the following groups are shown in the diagram: vehicle control (270 mM sucrose, black circles), lipid only at a dose of 21.7 mg/kg (dark green squares), ORC-1-siRNA-lipoplex at a dose of 2.8 mg/kg (blue diamond) and 1.4 mg/kg (light blue open diamond). The study consisted of two further groups with PKN3-siRNA-lipoplex.

The control group received 270 mM sucrose applied in the same treatment schedule than siRNA-lipoplexes, i.e. 300 μl i.v. bolus per 30 g mouse.

The experimental design is depicted in FIG. 7A.

The results of this experiment are shown in FIG. 7B which indicates the percentage of animals surviving between day 28 which is after the end of the treatment and day 108 post tumor transplantation.

From these results it can be taken that the formulation consisting of 2.8 mg/kg ORC1-3 siRNA molecules administered as the respective lipoplex providing for a total lipid amount of 21.7 mg/kg per injection was advantageous over the dosage providing 1.4 mg/kg ORC1-3 and a total lipid amount of 10.9 mg/kg.

The features of the present invention disclosed in the specification, the claims, the sequence listing and/or the drawings may both separately and in any combination thereof be material for realizing the invention in various forms thereof.

The invention claimed is:

1. A nucleic acid molecule comprising a double-stranded structure that is optionally covalently linked and each strand of the doubled-stranded structure has a length of 18-29 nucleotides, wherein the first stretch and/or the second stretch have a plurality of modified nucleotides having a modification at the 2' position wherein the first strand comprises a first stretch of contiguous nucleotides and said first stretch is at least partially complementary to a target nucleic acid, and wherein the second strand comprises a second stretch of contiguous nucleotides and said second stretch is at least partially complementary to the first stretch, wherein the first stretch consists of a nucleotide sequence according to SEQ ID NOS: 6, 34, 20 or 36 and the second stretch consists of a nucleotide sequence according to SEQ ID NOS: 7, 35, 21 or 37.

2. The nucleic acid according to claim 1, wherein the first stretch and/or the second stretch are: a) 18 to 29 consecutive nucleotides, b) 19 to 25 consecutive nucleotides or c) 19 to 23 consecutive nucleotides.

3. The nucleic acid molecule according to claim 1, wherein the first stretch and/or the second stretch have a plurality of modified nucleotides having a modification at the 2' position, wherein within the stretch each group of modified nucleotides is flanked on one or both sides by a flanking group of nucleotides, wherein the flanking nucleotide(s) forming the flanking group of nucleotides is/are either an unmodified nucleotide or a nucleotide having a modification different from the modification of the modified nucleotides, wherein the first stretch and/or the second stretch comprises at least two groups of modified nucleotides and at least two flanking groups of nucleotides.

4. The nucleic acid according to claim 1, wherein the first stretch and/or the second stretch contain a pattern of groups of modified nucleotides and/or a pattern of flanking groups of nucleotides, wherein the pattern is a positional pattern.

5. The nucleic acid according to claim 1, wherein the first stretch and/or the second stretch comprise at the 3' end a dinucleotide.

6. The nucleic acid according to claim 1, wherein the first and/or the second stretch have an overhang of 1 to 5 nucleotides at the 3' end.

7. The nucleic acid according to claim 1, wherein the length of the double-stranded structure is from about 16 to 27 nucleotide pairs.

8. A lipoplex comprising a liposome and a nucleic acid molecule comprising a double-stranded structure that is optionally covalently linked and each strand of the doubled-stranded structure has a length of 18-29 nucleotides,
wherein the first strand comprises a first stretch of contiguous nucleotides and said first stretch is at least partially complementary to a target nucleic acid, and
wherein the second strand comprises a second stretch of contiguous nucleotides and said second stretch is at least partially complementary to the first stretch,
wherein the first stretch consists of a nucleotide sequence according to SEQ ID NOS: 6, 34, 20 or 36 and the second stretch consists of a nucleotide sequence according to SEQ ID NOS: 7, 35, 21 or 37.

9. The lipoplex according to claim 8, wherein the liposome consists of
a) about 50 mol % β-arginyl-2,3-diaminopropionic acid-N-palmityl-N-oleyl-amide trihydrochloride;
b) about 48 to 49 mol % 1,2-diphytanoyl-sn-glycero-3-phosphoethanolamine (DPhyPE); and
c) about 1 to 2 mol % 1,2-distearoyl-sn-glycero-3-phosphoethanolamine-polyethylene-glycole.

10. A vector comprising or encoding a nucleic acid according to claim 1.

11. An isolated cell comprising a nucleic acid according to claim 1.

12. A composition, comprising a nucleic acid according to claim 1.

13. The composition according to claim 12, wherein the composition is a pharmaceutical composition, said pharmaceutical composition optionally further comprising a pharmaceutically acceptable vehicle.

14. The nucleic acid molecule according to claim 3, wherein said nucleotides are modified with amino, fluoro, methoxy, alkoxy or alkyl groups.

15. The nucleic acid molecule according to claim 14, wherein said nucleotides are modified with methoxy groups.

16. The lipoplex according to claim 8, wherein the nucleic acid has a first stretch and/or the second stretch that are: a) 18 to 29 consecutive nucleotides, b) 19 to 25 consecutive nucleotides or c) 19 to 23 consecutive nucleotides.

17. The lipoplex according to claim 8, wherein the first stretch and/or the second stretch of said nucleic acid molecule have a plurality of modified nucleotides having a modification at the 2' position, wherein within the stretch each group of modified nucleotides is flanked on one or both sides by a flanking group of nucleotides, wherein the flanking nucleotide(s) forming the flanking group of nucleotides is/are either an unmodified nucleotide or a nucleotide having a modification different from the modification of the modified nucleotides, wherein the first stretch and/or the second stretch comprises at least two groups of modified nucleotides and at least two flanking groups of nucleotides.

18. The lipoplex according to claim 8, wherein the first stretch and/or the second stretch of said nucleic acid contain a pattern of groups of modified nucleotides and/or a pattern of flanking groups of nucleotides, wherein the pattern is a positional pattern.

19. The lipoplex according to claim 8, wherein the first stretch and/or the second stretch of said nucleic acid comprise at the 3' end a dinucleotide.

20. The lipoplex according to claim 8, wherein the first and/or the second stretch of said nucleic acid molecule have an overhang of 1 to 5 nucleotides at the 3' end.

21. The lipoplex according to claim 8, wherein the length of the double-stranded structure is from about 16 to 27 nucleotide pairs.

\* \* \* \* \*

UNITED STATES PATENT AND TRADEMARK OFFICE
CERTIFICATE OF CORRECTION

PATENT NO. : 8,722,875 B2
APPLICATION NO. : 13/120430
DATED : May 13, 2014
INVENTOR(S) : Manfred Gossen et al.

It is certified that error appears in the above-identified patent and that said Letters Patent is hereby corrected as shown below:

In the Specification

Column 1,
Line 12, "thereof" should read --thereof.--.
Line 54, "Mcm2," should read --Mcm-2,--.

Column 4,
Lines 36-42,
"liposome.
    In a second embodiment of the third aspect which is also an embodiment of the first embodiment of the third aspect, the liposome consists of:
    In a second embodiment of the third aspect which is also an embodiment of the first embodiment of the third aspect, the liposome consists of
    a) about 50 mol%"
should read
--liposome.
    In a second embodiment of the third aspect which is also an embodiment of the first embodiment of the third aspect, the liposome consists of:
    a) about 50 mol%--.
Lines 66-67, "embodiment t of the" should read --embodiment of the--.

Column 5,
Line 39, "breast neoplasms, male," should read --breast neoplasms (male),--.
Line 40, "carcinoid tumor, carcinoma, carcinoma, Merkel cell carcinoma," should read
    --carcinoid tumor, carcinoma, Merkel cell carcinoma,--.
Lines 55-56, "lymphoma, lymphoma, non-hodgkin," should read
    --lymphoma, non-Hodgkin lymphoma,--.
Line 57, "melanoma, melanoma, amclanotic," should read
    --melanoma, amelanotic melanoma,--.

Signed and Sealed this
Thirteenth Day of January, 2015

Michelle K. Lee
*Deputy Director of the United States Patent and Trademark Office*

Column 6,
Lines 2-3, "sarcoma, sarcoma, Ewing's," should read --sarcoma, Ewing's sarcoma,--.
Line 17, "eethyma," should read --ecthyma,--.

Column 8,
Lines 65-66, "results form" should read --results from--.

Column 9,
Line 8, "(supra)" should read --(supra).--.

Column 12,
Line 29-32,
"respectively.
　　　In the following preferred nucleic acid molecules according to the present invention are defined by their sequences.
　　　In the following preferred nucleic acid molecules according to the present invention are defined by their sequences.
siRNA molecule ORC1-1 consisting of:"
should read
--respectively.
　　　In the following preferred nucleic acid molecules according to the present invention are defined by their sequences.
siRNA molecule ORC1-1 consisting of:--.

Column 13,
Line 35, "ORC1-3 consisting of" should read --ORC1-3 consisting of:--.

Column 14,
Line 18, "ORC1L-23-h-4 consisting of" should read --ORC1L-23-h-4 consisting of:--.
Line 35, "ORC1-5 consisting of" should read --ORC1-5 consisting of:--.
Line 44, "ORC1L-21-h-5 consisting of" should read --ORC1L-21-h-5 consisting of:--.

Column 16,
Line 18, "ORC1L-23-h-8 consisting of" should read --ORC1L-23-h-8 consisting of:--.

Column 18,
Line 1, "ORC1L-25-h-3 consisting of" should read --ORC1L-25-h-3 consisting of:--.

Column 23,
Line 39, "to of the first" should read --to the first--.
Line 43, "to of the first" should read --to the first--.

Column 24,
Line 48, "groups)" should read --group(s)--.

CERTIFICATE OF CORRECTION (continued)
U.S. Pat. No. 8,722,875 B2

Column 26,
Line 10, "both end." should read --both ends.--.
Line 47, "with in the" should read --within the--.

Column 28,
Line 59, "by, the" should read --by the--.

Column 31,
Line 34, "nucleic, acid" should read --nucleic acid--.

Column 33,
Line 32, "consisting of" should read --consisting of:--.

Column 42,
Line 27, "agents" should read --agents.--.

Column 43,
Line 19, "cells)" should read --cells).--.
Line 23, "Laboratories)" should read --Laboratories).--.

Column 45,
Line 39, "Table in" should read --Table 1 in--.

Column 46,
Line 14, "ucgaaguaguccgcguacg (SEQ.ID.No: 19)" should read
    --ucgaaguauuccgcguacg (SEQ.ID.No: 19)--.

Column 50,
Line 13, "siRNA$^{Orc1}$-lipoplexe" should read --siRNA$^{Orc1}$-lipoplex--.

UNITED STATES PATENT AND TRADEMARK OFFICE
CERTIFICATE OF CORRECTION

PATENT NO.        : 8,722,875 B2                              Page 1 of 1
APPLICATION NO.   : 13/120430
DATED             : May 13, 2014
INVENTOR(S)       : Gossen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 10 days.

Signed and Sealed this

Twenty-ninth Day of September, 2015

Michelle K. Lee
*Director of the United States Patent and Trademark Office*

UNITED STATES PATENT AND TRADEMARK OFFICE
CERTIFICATE OF CORRECTION

PATENT NO.       : 8,722,875 B2
APPLICATION NO.  : 13/120430
DATED            : May 13, 2014
INVENTOR(S)      : Manfred Gossen et al.

It is certified that error appears in the above-identified patent and that said Letters Patent is hereby corrected as shown below:

In The Specification

Column 1,
Line 12, "thereof" should read --thereof.--.
Line 54, "Mcm2," should read --Mcm-2,--.

Column 4,
Lines 36-42,
"liposome.
    In a second embodiment of the third aspect which is also an embodiment of the first embodiment of the third aspect, the liposome consists of:
    In a second embodiment of the third aspect which is also an embodiment of the first embodiment of the third aspect, the liposome consists of
    a) about 50 mol%"
should read
--liposome.
    In a second embodiment of the third aspect which is also an embodiment of the first embodiment of the third aspect, the liposome consists of:
    a) about 50 mol%--.
Lines 66-67, "embodiment t of the" should read --embodiment of the--.

Column 5,
Line 39, "breast neoplasms, male," should read --breast neoplasms (male),--.
Line 40, "carcinoid tumor, carcinoma, carcinoma, Merkel cell carcinoma," should read
    --carcinoid tumor, carcinoma, Merkel cell carcinoma,--.
Lines 55-56, "lymphoma, lymphoma, non-hodgkin," should read
    --lymphoma, non-Hodgkin lymphoma,--.

This certificate supersedes the Certificate of Correction issued January 13, 2015.

Signed and Sealed this
Nineteenth Day of January, 2016

Michelle K. Lee
*Director of the United States Patent and Trademark Office*

CERTIFICATE OF CORRECTION (continued)
U.S. Pat. No. 8,722,875 B2

Column 5,
Line 57, "melanoma, melanoma, amelanotic," should read
    --melanoma, amelanotic melanoma,--.

Column 6,
Lines 2-3, "sarcoma, sarcoma, Ewing's," should read --sarcoma, Ewing's sarcoma,--.
Line 17, "eethyma," should read --ecthyma,--.

Column 8,
Lines 65-66, "results form" should read --results from--.

Column 9,
Line 8, "(supra)" should read --(supra).--.

Column 12,
Line 29-32,
"respectively.
    In the following preferred nucleic acid molecules according to the present invention are defined by their sequences.
    In the following preferred nucleic acid molecules according to the present invention are defined by their sequences.
siRNA molecule ORC1-1 consisting of:"
should read
--respectively.
    In the following preferred nucleic acid molecules according to the present invention are defined by their sequences.
siRNA molecule ORC1-1 consisting of:--.

Column 13,
Line 35, "ORC1-3 consisting of" should read --ORC1-3 consisting of:--.

Column 14,
Line 18, "ORC1L-23-h-4 consisting of" should read --ORC1L-23-h-4 consisting of:--.
Line 35, "ORC1-5 consisting of" should read --ORC1-5 consisting of:--.
Line 44, "ORC1L-21-h-5 consisting of" should read --ORC1L-21-h-5 consisting of:--.

Column 16,
Line 18, "ORC1L-23-h-8 consisting of" should read --ORC1L-23-h-8 consisting of:--.

Column 18,
Line 1, "ORC1L-25-h-3 consisting of" should read --ORC1L-25-h-3 consisting of:--.

Column 23,
Line 39, "to of the first" should read --to the first--.
Line 43, "to of the first" should read --to the first--.

CERTIFICATE OF CORRECTION (continued)
U.S. Pat. No. 8,722,875 B2

Column 24,
Line 48, "groups)" should read --group(s)--.

Column 26,
Line 10, "both end." should read --both ends.--.
Line 47, "with in the" should read --within the--.

Column 28,
Line 59, "by, the" should read --by the--.

Column 31,
Line 34, "nucleic, acid" should read --nucleic acid--.

Column 33,
Line 32, "consisting of" should read --consisting of:--.

Column 42,
Line 27, "agents" should read --agents.--.

Column 43,
Line 19, "cells)" should read --cells).--.
Line 23, "Laboratories)" should read --Laboratories).--.

Column 45,
Line 39, "Table in" should read --Table 1 in--.

Column 46,
Line 14, "ucgaaguaguccgcguacg (SEQ.ID.No: 19)" should read
    --ucgaaguauuccgcguacg (SEQ.ID.No: 19)--.

Column 50,
Line 13, "siRNA$^{Orc1}$-lipoplexe" should read --siRNA$^{Orc1}$-lipoplex--.